United States Patent [19]

Albert et al.

[11] Patent Number: 4,617,296

[45] Date of Patent: Oct. 14, 1986

[54] 3-O-ACYLATED DERIVATIVES OF (+)-CYANIDAN-3-OL

[75] Inventors: Alban Albert, Avully; Pierre Courbat, Nyon; André Weith, Prangins, all of Switzerland

[73] Assignee: Ciba-Geigy Corporation, Ardsley, N.Y.

[21] Appl. No.: 626,823

[22] Filed: Jul. 2, 1984

Related U.S. Application Data

[60] Continuation of Ser. No. 422,110, Sep. 23, 1982, abandoned, which is a division of Ser. No. 182,169, Aug. 28, 1980, abandoned, which is a division of Ser. No. 962,743, Nov. 21, 1978, Pat. No. 4,255,336.

[30] Foreign Application Priority Data

Nov. 25, 1977 [CH] Switzerland .................. 14479/77
Mar. 17, 1978 [CH] Switzerland .................. 2937/78

[51] Int. Cl.$^4$ ..................... A61K 31/35; C07D 311/62
[52] U.S. Cl. .................... 514/100; 514/337; 514/456; 546/269; 549/220; 549/399
[58] Field of Search ............. 549/399, 220; 514/456, 514/337, 100; 546/269

[56] References Cited

U.S. PATENT DOCUMENTS 4,166,861 9/1979 Bonati et al. .................. 549/399

FOREIGN PATENT DOCUMENTS 2711927 10/1977 Fed. Rep. of Germany .

OTHER PUBLICATIONS

Cetta et al., Ital. J. Biochem., 26, 317 (1977).
Weinges et al., Liebigs Ann. Chem., 714, 193 (1968).
Freundberg et al., Ber., 55, 1734 (1922).

Primary Examiner—Nicky Chan
Attorney, Agent, or Firm—Michael W. Glynn; Irving M. Fishman

[57] ABSTRACT

The subject of the present invention is new O-substituted derivatives of (+)-cyanidan-3-ol corresponding to the general formula I

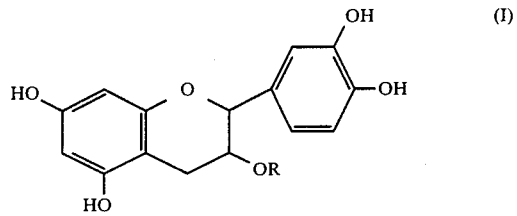

in which R represents an optionally substituted hydrocarbon radical; an acyl radical of an organic carboxylic acid containing at least 2 carbon atoms, of a carbonic acid or of an organic sulphonic acid; or a radical of an inorganic acid containing at least one oxygen atom, with the exception of a glucosidic radical, and the salts thereof, a process for the preparation thereof as well as their application in therapeutics and medicaments containing these new products.

These compounds have a valuable activity in the prevention of hepatic necrosis and also inhibit lipoperoxidation. In addition, they are capable of acting on the fibrillation of collagen.

19 Claims, No Drawings

3-O-ACYLATED DERIVATIVES OF (+)-CYANIDAN-3-OL

This is a continuation of application Ser. No. 422,110 filed on Sept. 23, 1982, abandoned, which in turn is a divisional of Ser. No. 182,169, filed on Aug. 28, 1980, abandoned, which in turn is a divisional of application Ser. No. 962,743, filed Nov. 21, 1978, now U.S. Pat. No. 4,255,336, issued on Mar. 10, 1981.

The subject of the present invention is new O-substituted derivatives of (+)-cyanidan-3-ol, especially 3-O-substituted derivatives of (+)-cyanidan-3-ol corresponding to the formula I

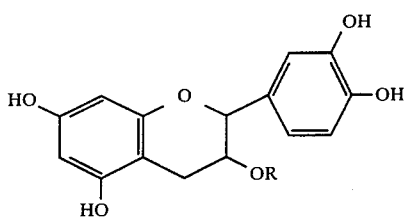

in which
R represents an optionally substituted hydrocarbon radical; an acyl radical of an organic carboxylic acid containing at least 2 carbon atoms, of a carbonic acid, or of an organic sulphonic acid; or a radical of an inorganic acid containing at least one oxygen atom, with the exception of a glucosidic radical,
and the salts thereof, a process for the preparation thereof, as well as their application in therapeutics and medicaments containing these new products.

In the following, "lower" radicals are, in particular, radicals containing up to 7 carbon atoms and, more especially, up to 4 carbon atoms.

An optionally substituted hydrocarbon radical represented by the group R is, for example, an aliphatic, cycloaliphatic, cycloaliphatic-aliphatic, aromatic, aromatic-aliphatic, heterocylic or heterocyclic-aliphatic hydrocarbon radical. These radicals may be substituted and contain from 1 to 24 carbon atoms.

An acyl radical of a carboxylic acid is, in particular, an aliphatic, cycloaliphatic, cycloaliphatic-aliphatic, aromatic, aromatic-aliphatic, heterocyclic or heterocyclic-aliphatic acid radical containing 2 to 24 carbon atoms which is optionally substituted.

A carbonic acid radical represented by the group R is, for example, a radical of esterified or amidated carbonic acid.

An organic sulphonic acid radical is, in particular, an optionally substituted aliphatic, aromatic or aromatic-aliphatic sulphonic acid radical containing from 1 to 12 carbon atoms.

An inorganic acid radical is especially the radical of an acid having as principal atom an atom of one of the groups III, IV, V or VI of Mendelejeff's Periodic Table and especially of periods 1 and 2. Examples of principal atoms are sulphur, phosphorus, boron and nitrogen.

An aliphatic hydrocarbon radical is especially a saturated hydrocarbon radical, such as an alkyl radical, or an unsaturated hydrocarbon radical, such as an alkenyl or alkynyl radical. They may be linear or branched-chained. Such radicals may, if desired, be monosubstituted, disubstituted or polysubstituted by functional groups.

An optionally substituted cycloaliphatic or cycloaliphatic-aliphatic hydrocarbon radical is, for example, a monocyclic, bicyclic or polycyclic cycloalkyl or cycloalkenyl radical, or a cycloalkyl-lower alkyl, cycloalkenyl-lower alkyl, cycloalkyl-lower alkenyl or cycloalkenyl-lower alkenyl radical, in which a cycloalkyl radical contains, for example, up to 12, for example, from 3 to 8 preferably from 3 to 6, ring carbon atoms, while a cycloalkenyl radical has, for example, up to 12, for example, from 3 to 8 and preferably 5 or 6, ring carbon atoms as well as one or two double bonds, while the aliphatic moiety of a cycloaliphatic-aliphatic radical may, for example, contain up to 7, preferably up to 4, carbon atoms. The above cycloaliphatic or cycloaliphatic-aliphatic radicals may, if desired, be monosubstituted, disubstituted or polysubstituted.

An optionally substituted aromatic hydrocarbon radical is, for example, a monocyclic, bicyclic or polycyclic aromatic hydrocarbon radical, in particular a phenyl radical, but may be a naphthyl radical, which may, if desired, be monosubstituted, disubstituted or polysubstituted.

An optionally substituted aromatic-aliphatic hydrocarbon radical is, for example, an optionally substituted aliphatic hydrocarbon radical having up to three optionally substituted monocyclic, bicyclic or polycyclic aromatic hydrocarbon radicals and it represents especially a phenyl-lower alkyl radical, but may be a phenyl-lower alkenyl radical or a phenyl-lower alkynyl radical and such radicals may contain, for example, from 1 to 3 phenyl groups and may, if desired, be monosubstituted, disubstituted or polysubstituted in the aromatic and/or aliphatic moiety.

A heterocyclic radical is, in particular, a monocyclic radical but may be a bicyclic or polycyclic radical, preferably a saturated or unsaturated aza-, thia-, oxa-, thiaza-, oxaza- or diaza-cyclic radical, for example of an aromatic nature, having preferably from 2 to 7 carbon atoms and which may, if desired, be monosubstituted, disubstituted or polysubstituted. The aliphatic moiety in a heterocyclic-aliphatic radical may, for example, have the meaning given for the aliphatic moiety in the corresponding cycloaliphatic-aliphatic or aromatic-aliphatic radicals.

The acyl radicals R of an aliphatic carboxylic acid are especially radicals of alkanecarboxylic acids, especially of lower alkanecarboxylic acids, but may be radicals of alkenecarboxylic acids, especially of lower alkenecarboxylic acids, and also of lower alkane dicarboxylic acids or of lower alkenedicarboxylic acids.

The acyl radicals R of a cycloaliphatic, cycloaliphatic-aliphatic, aromatic, aromatic-aliphatic, heterocyclic or heterocyclic-aliphatic carboxylic acid have, in the ring and/or the aliphatic radical, the meaning given above for the cycloaliphatic, aromatic or heterocyclic radicals or the corresponding aliphatic radicals. They may carry substituents.

The acyl radicals R of an esterified or amidated carbonic acid are especially aliphatic, aromatic or araliphatic esters of carbonic acid, such as a lower alkoxycarbonyl, aryloxycarbonyl or aryl-lower alkoxycarbonyl group or of a carbamic acid preferably mono- or di-substituted by aliphatic, aromatic or araliphatic radicals.

The functional groups appearing as complementary substituents of one of the radicals mentioned above are, for example, free, etherified or esterified hydroxy or mercapto groups, such as lower alkoxy, lower alkenyloxy, lower alkylmercapto groups or optionally substituted phenylmercapto groups or phenyl-lower alkylmercapto groups, lower alkoxycarbonyloxy groups or lower alkanoyloxy groups as well as halogen atoms, and also nitro groups, optionally substituted amino groups, acyl groups, such as lower alkanoyl groups, or optionally functionally modified carboxy groups, such as lower alkoxycarbonyl groups, optionally N-substituted carbamoyl groups, or cyano groups. The aromatic or heterocyclic radicals may also carry as substituents alkyl radicals, preferably lower alkyl radicals.

Etherified hydroxy groups should be understood as meaning especially lower alkoxy groups as well as substituted lower alkoxy groups, such as halogeno-lower alkoxy groups, as well as lower alkenyloxy groups, lower alkylenedioxy groups, cycloalkoxy groups, phenyloxy groups, phenyl-lower alkoxy groups, or lower alkoxy groups substituted by monocyclic mono-aza-, mono-oxa- or mono-thia-cyclic groups of aromatic nature, such as pyridyl-lower alkoxy groups, furyl-lower alkoxy groups or thienyl-lower alkoxy groups.

As etherified mercapto groups there should be mentioned lower alkylmercapto groups, phenylmercapto groups or phenyl-lower alkylmercapto groups.

The esterified hydroxy groups are especially halogen atoms as well as lower alkanoyloxy groups.

The substituted amino groups are monosubstituted or disubstituted amino groups in which the substituents represent especially optionally substituted monovalent or bivalent aliphatic, cycloaliphatic, cycloaliphatic-aliphatic, aromatic or araliphatic hydrocarbon radicals as well as acyl groups. Such amino groups are, in particular, lower alkylamino groups or di-lower alkylamino groups or lower alkyleneamino groups optionally interrupted by hetero atoms, such as oxygen atoms, sulphur atoms or, if desired, by optionally substituted nitrogen atoms, for example by lower alkyl groups, as well as acylamino groups, in particular lower alkanoylamino groups.

In the above and the following the general terms may have the following meanings:

An alkyl radical is preferably a lower alkyl radical, for example a methyl, ethyl, n-propyl, isopropyl, n-butyl, isobutyl, secondary butyl or tertiary butyl radical but also a pentyl, isopentyl, n-hexyl, isohexyl, n-heptyl, octyl, nonyl, decyl, undecyl, dodecyl, tricosyl or tetracosyl radical and the isomers thereof, while an alkenyl radical, preferably a lower alkenyl radical, may, for example, be a vinyl, allyl, n-propenyl, isopropenyl, 2- or 3-methallyl or 3-butenyl group, and an alkynyl radical may be, for example, a propargyl or 2-butyryl radical.

The substituted aliphatic hydrocarbon radicals include, preferably, hydroxy groups, lower alkoxy groups or halogen atoms and are especially hydroxy-lower alkoxy or lower alkoxy-lower alkoxy radicals in which the hydroxy groups or the lower alkoxy groups are separated preferably by at least two carbon atoms from the oxygen atom carrying a lower aliphatic radical substituted in this manner, such as 2-hydroxyethyl, 2-hydroxypropyl, 3-hydroxypropyl, 2,3-dihydroxypropyl, 2-methoxyethyl, 2-ethoxyethyl, 2-methoxypropyl, 3-methoxypropyl or 3-ethoxypropyl radicals as well as hydroxymethyl radicals.

A cycloalkyl radical is, for example, a cyclopropyl, cyclobutyl, cyclopentyl, cyclohexyl or cycloheptyl radical as well as an adamantyl group, and a cycloalkenyl group, for example a 2- or 3-cyclopentenyl, a 1-, 2- or 3-cyclohexenyl group or a 3-cycloheptenyl group, as well as a 2-cyclopropenyl group. A cycloalkyl-lower alkyl radical or cycloalkyl-lower alkenyl radical is, for example, a cyclopropyl-, cyclopentyl-, cyclohexyl- or cycloheptyl-methyl, -1,1- or -1,2-ethyl, -1,1-, -1,2- or -1,3-propyl, -vinyl or -allyl radical, while a cycloalkenyl-lower alkyl or cycloalkenyl-lower alkenyl radical represents, for example, a 1-, 2- or 3-cyclopentenyl-, 1-, 2- or 3-cyclohexenyl- or 1-, 2- or 3-cycloheptenyl-methyl, -1,1-, or -1,2-ethyl, -1,1-, -1,2- or -1,3-propyl, -vinyl or -allyl radical.

A naphthyl radical is a 1- or 2-naphthyl radical while a diphenyl radical is, for example, a 4-diphenyl radical.

A phenyl-lower alkyl or phenyl-lower alkenyl radical is especially a benzyl radical as well as a 1- or 2-phenylethyl, 1-, 2- or 3-phenylpropyl, diphenylmethyl, trityl, 1- or 2-naphthylmethyl, styryl or cinnamyl radical. A substituted phenyl-lower alkyl radical is especially a benzyl radical that may be monosubstituted, disubstituted or polysubstituted in the phenyl nucleus and in the case of multiple substitution different substituents may be present. The substituents are, in particular, halogen atoms or lower alkyl groups as well as lower alkoxy groups or trifluoromethyl groups, while the benzyl radicals in the substituted nucleus carry a substituent, preferably in the para-position.

The heterocyclic radicals are, for example, monocyclic mono-aza-, mono-thia- or mono-oxa-cyclic radicals of an aromatic nature, such as pyridyl radicals, for example, 2-pyridyl, 3-pyridyl or 4-pyridyl radicals, thienyl radicals, for example, 2-thienyl radicals, or furyl radicals, for example, 2-furyl radicals, or bicyclic mono-aza-cyclic radicals of an aromatic nature, such as quinolinyl radicals, for example, 2-quinolinyl radicals or 4-quinolinyl radicals, or isoquinolinyl radicals, for example, 1-isoquinolinyl radicals, or monocyclic thiaza- or oxaza-cyclic radicals of an aromatic nature as well as diaza-cyclic radicals of an aromatic nature, such as oxazolyl, isoxazolyl, thiazolyl or isothiazolyl radicals, and also pyrimidinyl radicals. Aliphatic heterocyclic radicals are lower alkyl or lower alkenyl radicals containing heterocyclic radicals, in particular those indicated above.

The acyl radicals of alkanecarboxylic acids are, in particular, those of propionic, butyric, isobutyric and valeric acid and the higher homologues up to stearic acid; those of alkanedicarboxylic acids containing, for example, from 2 to 10, preferably from 3 to 6, carbon atoms; or of alkenedicarboxylic acids containing, for example, from 4 to 7 carbon atoms, for example, those of 2-methylsuccinic, glutaric, 3-methylglutaric, 3-ethylglutaric, adipic, pimelic, suberic, azelaic or sebacic acid, preferably malonic and succinic acids; there should be mentioned as acyl radicals of unsaturated aliphatic acids those of acrylic, propiolic, methacrylic, crotonic or oleic acid, especially of maleic acid or fumaric acid.

The acyl radicals of carbocylic acids are especially those of cyclohexanecarboxylic acid and benzoic acid which may be substituted, for example, by a lower alkyl group, such as methyl, by an alkoxy group, such as methoxy or ethoxy or by a carboxy group; of these there should be mentioned those of phthalic, isophthalic, terephthalic, cinnamic or toluic acid, as well as those of 1- or 2-naphthoic acid or 1,2-cyclohexanedicarboxylic acid.

The acyl radicals of heterocyclic acids are, for example, those of furoic, thenoic, nicotinic, isonicotinic or picolinic acid.

A lower alkoxycarbonyl group is, for example, a methoxycarbonyl, ethoxycarbonyl, n-propoxycarbonyl, isopropoxycarbonyl, tert.-butoxycarbonyl or tert.-pentyloxycarbonyl group.

The optionally N-substituted carbamoyl groups are, for example, N-lower alkyl- or N,N-di-lower alkylcarbamoyl groups, such as N-methyl-, N-ethyl-, N,N-dimethyl- or N,N-diethyl-carbamoyl groups, N-aryl-, N,N-diaryl- or N-aryl-N-alkyl-carbamoyl groups, such as N-phenyl-, N,N-diphenyl- or N-phenyl-N-methyl- or -ethylcarbamoyl groups, substituted or unsubstituted in the phenyl nucleus.

A lower alkoxy group is, for example, a methoxy, ethoxy, n-propoxy, isopropoxy, n-butoxy, isobutoxy, sec.-butoxy, tert.-butoxy, n-pentyloxy or tert.-pentyloxy group.

A lower alkenyloxy group is, for example, a vinyloxy or allyloxy group.

A lower alkylenedioxy group is, for example, a methylenedioxy or ethylenedioxy group as well as an isopropylidenedioxy group.

A cycloalkoxy group is, for example, a cyclopentyloxy, cyclohexyloxy or adamantyloxy group.

A phenyl-lower alkoxy group is, for example, a benzyloxy or 1- or 2-phenylethoxy group.

A pyridyl-lower alkoxy group is, for example, the 2-, 3- or 4-pyridylmethoxy group.

A furyl-lower alkoxy group is, for example, the furfuryloxy group.

A thienyl-lower alkoxy group is, for example, the 2-thienyloxy group.

A lower alkylmercapto group is, for example, the methylmercapto or ethylmercapto group.

A phenyl-lower alkylmercapto group is, for example, the benzylmercapto or 1- or 2-phenylethylmercapto group.

A halogen atom is, for example, a bromine or iodine and especially a chlorine or fluorine atom.

A mono- or di-lower alkylamino is, for example, the methylamino, dimethylamino, ethylamino or diethylamino group.

A lower alkyleneamino group optionally interrupted by hetero atoms is, for example, a pyrrolidino, piperidino, morpholino, thiamorpholino or 4-methylpiperazino group.

A lower alkanoylamino group is, for example, the acetylamino or propionylamino group.

The acyl radicals of mineral acids are, for example, those of sulphonic, sulphinic, sulphenic, phosphoric, boric or nitric acid.

The compounds of the invention comprising a radical containing a salt-forming group may also be in the form of salts.

The salts of the compounds containing a free carboxy group are, for example, metal salts, in particular alkali metal salts, for example, sodium or potassium salts, as well as alkaline-earth metal salts, for example, magnesium or calcium salts, as well as salts of transition metals, for example, zinc, copper, iron, silver or mercury salts, or ammonium salts, for example, those of ammonia and organic bases, such as tri-lower alkylamines, for example, trimethylamine or triethylamine, in particular pharmaceutically acceptable non-toxic salts of the above type.

The new compounds comprising basic groups may also be in the form of addition salts with acids, in particular in the form of pharmaceutically acceptable non-toxic salts, for example with mineral acids such as hydrochloric acid, hydrobromic acid, sulphuric acid or phosphoric acid, or with organic sulphonic or carboxylic acids, for example, aliphatic, cycloaliphatic, cycloaliphatic-aliphatic, aromatic, araliphatic, heterocyclic or heterocyclic-aliphatic acids, for example, acetic, propionic, succinic, glycolic, lactic, malic, tartaric, citric, ascorbic, maleic, phenylacetic, benzoic, 4-aminobenzoic, anthranilic, 4-hydroxybenzoic, salicylic, aminosalicylic, embonic or nicotinic acid, as well as methanesulphonic, ethanesulphonic, 2-hydroxyethanesulphonic, phenylsulphonic, 4-methylphenylsulphonic, naphthalenesulphonic, sulphanilic or cyclohexylsulphamic acids.

The new compounds containing basic groups may be in the form of their quaternary ammonium compounds.

The new compounds have valuable pharmacological properties. In particular, they have a useful activity in the prevention of hepatic necrosis and inhibit lipoperoxidation. These substances are also capable of inhibiting both the degradation of collagen and the activity of lysosomal enzymes by increasing the stability of the membrane of the lysosomes. These derivatives are also capable of influencing vascular permeability and tonus.

The value of the new compounds is evident in the treatment of hepatic diseases such as acute hepatites (viral, alcoholic, toxic) steatoses and chronic hepatites, in particular of alcoholic origin. The value of these substances is also obvious in the treatment of diseases involving a deterioration in the connective tissue, in particular genetic diseases of the collagen, such as the Ehlers-Danlos diseases, Marfan's syndrome, cutis laxa, osteogenisis imperfecta, but also scoliosis, osteoporosis, scleroderma, parodontosis, the healing of sores, in particular decubitus ulcers, and also various forms of rheumatism, in particular arthroses. The value of these new substances is also shown in circulatory, venous and arterial diseases.

Thus, for example, the effect on the normal or pathological metabolism of the hepatocytes of live rats can be shown on rats' hepatocytes isolated according to Berry and Friend's technique [J. Cell. Biol. 43, 506–520 (1969)] and incubated in 2 ml of physiological Krebs-Ringer solution in the presence of the new products in quantities varying from 0.5 to 5 mg and to which solution different hepatotoxic substances are added, or the inhibition of lipoperoxidation by carbon tetrachloride may be demonstrated by the method of Comporti, Sacconi and Danzani [Enzymologia 28, 185–203 (1965)] and the intensity of lipoperoxidation in the presence of the new products at the rate of 5 to 50 μg per 4 ml is evaluated by the quantity of malonic dialdehyde formed. The modification of the experimental hepatitis induced by galactosamine, carbon tetrachloride or ethanol may be demonstrated in rats pretreated orally or intra-peritoneally with the new products at doses varying from 100 to 500 mg/kg in cases of acute or chronic disease and in prophylactic or curative treatment. In the investigations of acute diseases the animals are killed 24 or 48 hours after the administration of the toxic substance and the state of hepatic functioning is evaluated by the following tests: BSP clearance, level of bilirubin in the plasma, level of transaminase in the plasma, total levels of triglycerides and lipids in the liver and in the serum and the level of lipoproteins in the serum. These substances also prove capable of promoting the process of hepatic regeneration and exercising an immunostimulant effect.

The activity of the new products in the protection of the connective tissue may be demonstrated by the inhibition of the degradation of collagen by collagenase with quantities of substance of from 0.1 to 5 mg per 2 ml, or by the inhibition of the activity of lysosomal enzymes and the increase in the stability of the membrane of the lysosomes with 0.05 to 0.2 mg of the new products per 1 ml according to P. Niebès and Ponard, [Biochem. Pharmacol. 24, 905 (1975)] or also by experimental lathyrism in rats which have been given toxic aminoacetonitrile per os at a dose of 100 mg/kg/day or iminodipropionitrile subcutaneously at a dose of 250 mg/kg/day for 7 days or $\beta$-aminopropionitrile orally at a dose of 600 mg/kg/day for 3 weeks and which have been given orally doses of from 100 to 500 mg/kg/day of the new products for three weeks before, during or after intoxication. At doses administered parenterally and orally varying from 100 to 500 mg/kg these substances prove to be capable, in the case of animals, of (a) reducing the experimental oedema induced by galactosamine and dextran, (b) reducing the capillary permeability in rats, measured by the diffusion of Trypan Blue [technique of V. L. Beach and B. G. Steinetz, J. pharmacol. Exp. Ther. 131, 400 (1961)] or in the chaps of a hamster subjected to a lesion induced by bradykinin, histamine or serontonin, (c) reducing the retroauricular venous flow in the ear of a rabbit, (d) promoting tissular lactic purification in the ischemic paw of a dog.

The activity of these new substances had not been observed hitherto in respect of these indications. It is known at the present time that (+)-cyanidan-3-ol has hepatoprotective effects but it is surprising that these new derivatives have an unexpected and superior activity to that of (+)-cyanidan-3-ol.

The present invention relates notably to compounds of the formula I, in which R is an aliphatic, cycloaliphatic, cycloaliphatic-aliphatic, aromatic, aromatic-aliphatic, heterocyclic or heterocyclic-aliphatic hydrocarbon radical;

a radical of an aliphatic, cycloaliphatic, cycloaliphatic-aliphatic, aromatic, aromatic-aliphatic, heterocyclic or heterocyclic-aliphatic carboxylic acid; a radical of an esterified or amidated carbonic acid;

a radical of an aliphatic, aromatic or aromatic-aliphatic sulphonic acid; or a radical of an inorganic acid having as principal atom a sulphur, phosphorus, boron or nitrogen atom;

and the salts thereof.

The present invention relates especially to compounds of the formula I in which R is an alkyl or alkenyl radical which is unsubstituted or substituted by hydroxy, lower alkanoyloxy, lower alkoxy, lower alkanoyl, cyano, amino, mono- or di-lower alkylamino, lower alkyleneamino, oxa- or aza-lower alkyleneamino, amido or mono- or di-lower alkylamido groups or by halogen atoms;

a cycloaliphatic radical containing from 3 to 6 ring carbon atoms which is unsubstituted or substituted by one or more hydroxy, lower alkoxy, lower alkyl, carboxy, oxo, lower alkanoylamino, mono- or di-lower alkylamino or lower alkoxycarbonyl groups;

a lower cycloaliphatic-alkyl radical containing from 3 to 6 ring carbon atoms which is unsubstituted or substituted by at least one lower alkyl group;

a phenyl or naphthyl radical which is unsubstituted or mono-, di- or tri-substituted by hydroxy, lower alkoxy, carboxy, lower alkoxycarbonyl, nitro, amino or mono- or di-lower alkylamino groups, or by halogen atoms;

a phenyl-lower alkyl or naphthyl-lower alkyl radical or phenyl-lower alkenyl or naphthyl-lower alkenyl radical which is unsubstituted or mono-, di- or tri-substituted in the aromatic nucleus by hydroxy, lower alkoxy, carboxy, lower alkoxycarbonyl, lower alkanoyl, nitro, amino, mono- or di-lower alkylamino, amido or mono- or di-lower alkylamido groups or by halogen atoms;

a saturated or unsaturated aza-, thia-, oxa-, thiaza-, oxaza- or diaza-cyclic radical which may be condensed to a phenyl nucleus and has from 2 to 7 carbon atoms in the heterocyclic nucleus, and which may be mono-, di- or polysubstituted by lower alkyl, hydroxy, lower alkoxy, nitro, carboxy, lower alkoxycarbonyl or lower alkanoyloxy groups;

a heterocyclic-lower alkyl radical of which the heterocycle is one of those described above;

a radical of an alkanecarboxylic acid, a lower alkenecarboxylic acid, a lower alkanedicarboxylic acid, a lower alkenedicarboxylic acid or a lower cycloalkanecarboxylic acid which is unsubstituted or substituted by one or more hydroxy, lower alkoxy, carboxy, lower alkoxycarbonyl, lower alkyl, lower alkanoyl or oxo groups or by halogen atoms;

a benzoyl or naphthoyl radical optionally substituted by hydroxy, lower alkoxy, lower alkanoyloxy, carboxy, lower alkoxycarbonyl, nitro or amino groups or by halogen atoms;

a radical of a phenyl-lower alkanoic or naphthyl-lower alkanoic acid which is unsubstituted or substituted in the aromatic nucleus by one or more hydroxy, lower alkoxy, carboxy, lower alkoxycarbonyl, lower alkanoyl, lower alkanoyloxy, nitro, amino or mono- or di-lower alkylamino groups or by halogen atoms;

a radical of an unsaturated or saturated aza-, thia-, oxa-, thiaza-, oxaza- or diaza-cyclic acid which may be condensed to a phenyl radical; a lower alkoxycarbonyl radical, a phenoxycarbonyl radical, a carbamoyl radical, optionally mono- or di-substituted by lower alkyl radicals or by phenyl or benzyl radicals optionally substituted in the phenyl nucleus by one or more hydroxy or lower alkoxy groups or by halogen atoms;

a radical of a lower alkylsulphonic acid or phenylsulphonic acid optionally substituted by one or more lower alkyl or lower alkoxy groups or by halogen atoms, or a radical of a phosphoric acid which is unsubstituted or esterified by one or two lower alkyl radicals or by one or two optionally substituted phenyl radicals, and the salts thereof.

The present invention relates notably to compounds of the formula I in which R is a lower alkyl radical which is unsubstituted or substituted by one, two or more hydroxy, lower alkoxy, lower alkanoyloxy, carboxy, cyano, lower alkanoyl, amino, mono- or di-lower alkylamino, lower alkyleneamino or oxa- or aza-alkyleneamino groups or by chlorine or fluorine atoms;

a cycloaliphatic radical containing 5 or 6 ring carbon atoms which is unsubstituted or substituted by hydroxy-lower alkyl, lower alkoxy, carboxy, lower alkoxycarbonyl, amino or mono- or di-lower alkylamino groups;

a cycloaliphatic-$C_{1-4}$alkyl radical, the ring of which contains 5 or 6 carbon atoms and which may be substituted by at least one alkyl radical having 1 to 4 carbon atoms;

a phenyl radical which is unsubstituted or mono-, di- or tri-substituted by hydroxy, $C_{1-4}$alkoxy, carboxy, nitro, amino or mono- or di-($C_{1-4}$alkyl)amino groups or by chlorine or fluorine atoms;

a benzyl, phenylethyl or phenylpropyl radical which is unsubstituted or mono-, di- or tri-substituted in the phenyl nucleus by hydroxy, $C_{1-4}$alkoxy, carboxy, ($C_{1-4}$alkoxy)carbonyl, nitro, amino, mono- or di-($C_{1-4}$alkyl)amino, or $C_{1-4}$alkyl groups or by chlorine or fluorine atoms;

a tetrahydropyranyl, pyridyl, quinolinyl or pyrimidyl radical optionally substituted by one or more nitro, amino or hydroxy groups; an alkanecarboxylic acid radical containing from 3 to 18 carbon atoms which is unsubstituted or substituted by one or more hydroxy, carboxy, ($C_{1-5}$alkoxy)carbonyl, $C_{1-5}$alkyl, amino or mono- or di-($C_{1-4}$alkyl)amino groups or by chlorine or fluorine atoms;

a cycloalkanecarboxylic acid radical having 3 to 6 ring carbon atoms which is unsubstituted or substituted by one or more hydroxy, carboxy, lower alkoxycarbonyl, amino or mono- or di-($C_{1-4}$alkyl)amino groups or by chlorine or fluorine atoms;

a cycloalkanealkanoic acid radical, the aliphatic chain having 1 to 4 carbon atoms and the ring having 3 to 6 ring carbon atoms;

a benzoyl radical which is unsubstituted or mono-, di- or tri-substituted by hydroxy, $C_{1-4}$-alkoxy, carboxy, ($C_{1-4}$alkoxy)carbonyl, $C_{1-4}$-alkanoyl, $C_{1-4}$-alkanoyloxy, nitro, amino or mono- or di-($C_{1-4}$alkyl)amino groups or by fluorine or chlorine atoms;

a phenylalkanoic acid radical of which the aliphatic chain contains 1 to 4 carbon atoms and of which the phenyl radical may be substituted as indicated above for the benzoyl group;

a radical of a nicotinic or isonicotinic acid;

a ($C_{1-4}$alkoxy)carbonyl radical; a carbamoyl radical optionally mono- or di-substituted by $C_{1-4}$alkyl groups or by phenyl groups unsubstituted or substituted by hydroxy, methoxy or ethoxy groups or by chlorine or fluorine atoms; or a phosphoric acid radical which is unsubstituted or mono- or di-methyl, ethyl or phenyl substituted, and the salts thereof.

The present invention relates particularly to compounds of the formula I in which R is a lower alkyl radical which is unsubstituted or substituted by one or two hydroxy, $C_{1-4}$alkoxy, carboxy, $C_{1-4}$alkanoyloxy, amino, mono- or di-($C_{1-4}$alkyl)amino or cyano groups;

a cycloaliphatic radical containing 5 or 6 ring carbon atoms which is unsubstituted or substituted by one or two hydroxy, $C_{1-4}$alkoxy, carboxy, $C_{1-4}$alkanoyloxy, amino, or di-lower alkylamino groups;

a cycloalkanealkyl radical of which the alkyl moiety contains 1 to 4 carbon atoms and of which the ring contains 5 or 6 carbon atoms;

a phenyl radical which is unsubstituted or mono-, di- or tri-substituted by hydroxy, methoxy, ethoxy, propoxy, amino or nitro groups;

a benzyl, phenylethyl or phenylpropyl radical which is unsubstituted or mono- or di-substituted in the phenyl nucleus by one or two hydroxy, methoxy, ethoxy, propoxy, carboxy, ($C_{1-4}$alkoxy)carbonyl, nitro, amino or mono- or di-($C_{1-4}$alkyl)amino groups or by chlorine or fluorine atoms;

a tetrahydropyranyl radical;

a pyridyl radical which is unsubstituted or substituted by a nitro, amino or hydroxy group;

an alkanecarboxylic acid radical containing 3 to 18 carbon atoms which is unsubstituted or substituted by one or more hydroxy, carboxy, ($C_{1-6}$alkoxy)carbonyl, $C_{1-5}$alkanoyl, amino, or mono- or di-($C_{1-4}$alkyl)amino groups or by chlorine or fluorine atoms;

a cycloalkanecarboxylic acid radical containing 5 or 6 ring carbon atoms which is unsubstituted or substituted by one, two or three hydroxy, carboxy, ($C_{1-4}$alkoxy)carbonyl, amino or mono- or di-($C_{1-4}$alkyl)amino groups or by chlorine or fluorine atoms;

a cycloalkanealkanoic acid radical of which the alkyl chain contains 2 to 4 carbon atoms and of which the cycloalkane moiety contains 5 or 6 ring carbon atoms;

a benzoyl radical which is unsubstituted or mono-, di- or tri-substituted by hydroxy, $C_{1-4}$alkoxy, carboxy, ($C_{1-4}$alkoxy)carbonyl, $C_{1-4}$alkanoyl, $C_{1-4}$alkanoyloxy, nitro, amino or mono- or di-($C_{1-4}$alkyl)amino groups or by chlorine or fluorine atoms;

a phenylalkanoic acid radical of which the aliphatic chain contains 1 to 4 carbon atoms and of which the phenyl nucleus is unsubstituted or substituted by one or two hydroxy, $C_{1-4}$alkoxy, amino, carboxy, ($C_{1-4}$alkoxy)carbonyl, $C_{1-4}$alkanoyl or $C_{1-4}$alkanoyloxy groups or by chlorine or fluorine atoms;

a nicotinic or isonicotinic acid radical;

a ($C_{1-4}$alkoxy)carbonyl radical;

a carbamoyl radical optionally mono-substituted by a $C_{1-4}$alkyl or phenyl radical;

or an unsubstituted phosphoric acid radical or a dimethyl-, diethyl- or monohydroxyphenylphosphoric acid radical.

The invention relates especially to the new compounds of the formula I described in the examples.

The new compounds may be obtained by methods known per se. Thus, they may be prepared in that, in compounds of the formula II

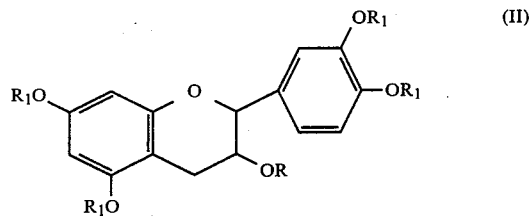

in which $R_1O$ represents a protected hydroxy group which is readily hydrolysable or hydrogenatable, the $OR_1$ groups are split into hydroxy groups and, if desired, in a resulting compound a radical R is modified by reduction and/or, if desired, a resulting salt is converted into the free compound or into another salt and/or, if desired, a resulting compound having a salt-forming group is converted into a salt.

In the compounds of the formula II the radical $R_1$ may therefore be a mono-, di- or poly-substituted lower alkyl radical; a lower alkenyl radical, an araliphatic radical which is unsubstituted or mono-, di- or tri-substituted in the aromatic nucleus; a radical of an aliphatic, aromatic or araliphatic carboxylic acid; a radical of a carbonic acid esterified by a lower alkyl radical; or a radical which, with the oxygen atom bonded to $R_1$, may or may not form a cyclic acetal.

When $R_1$ is a lower alkyl radical this radical contains preferably from 1 to 4 carbon atoms and is especially a methyl or ethyl radical. These groups may be substituted by lower alkoxy groups, preferably a methoxy or ethoxy group, or lower alkoxyethoxy groups, especially a methoxyethoxy group.

When $R_1$ is a lower alkenyl radical this radical contains preferably 2 to 5 carbon atoms and is especially allyl, methallyl, buten-2-yl, or penten-2-yl.

When the substituent $R_1$ is an araliphatic radical, especially a benzyl radical, this radical may be substituted in various ways, for example, by one or more $C_{1-4}$alkyl radicals, preferably methyl, ethyl, isopropyl and tert.-butyl groups; by one or more halogen atoms, preferably chlorine, bromine or fluorine; by one or more alkoxy groups, such as methoxy or ethoxy; or by a cyano group. These various substituents may occupy, simultaneously or not, the ortho and para positions, preferably the para position. When the substituent in the radical $R_1$ is of the second order, for example a nitro group, it is preferable that it should be in the meta position.

When $R_1$ is an aliphatic acyl radical the aliphatic moiety may be a $C_{1-4}$alkyl group and preferably a methyl or ethyl group optionally substituted by an alkoxy group, such as a methoxy group. If $R_1$ is an aromatic or araliphatic acyl radical the aryl moiety may be a phenyl radical substituted in various ways and the aliphatic radical may be a $C_{1-4}$alkyl radical.

When $R_1$ is an alkoxycarbonyl radical the alkyl moiety may itself be substituted by an aryl radical, which may itself be substituted in various ways, or by halogen atoms.

When $R_1$ forms an acetal with the oxygen atom bonded to $R_1$, this acetal may be linear or cyclic, such as, for example, the pyranyl group for $R_1$.

Of the radicals of the formula $R_1$ those which should be mentioned above all are, for example, the allyl, methylallyl, ethylallyl, buten-2-yl, penten-2-yl, methoxymethyl, ethoxymethyl, methoxyethoxymethyl, acetonyl, propionylmethyl, cinnamyl, phenacyl, benzyl, 2-methylbenzyl, 4-methylbenzyl, 4-tert.-butylbenzyl, 4-bromobenzyl, 4-fluorobenzyl, 4-chlorobenzyl, 4-methoxybenzyl, 4-ethoxybenzyl, 3-nitrobenzyl, 3,5-dinitrobenzyl, 4-cyanobenzyl, 4-chloro- or bromo- or phenylphenacyl or methoxycarbonyl, ethoxycarbonyl, 2,2,2-trichloroethoxycarbonyl or phenoxycarbonyl.

The groups $OR_1$ may be split by hydrolysis or by hydrogenation.

The substances may in fact be hydrolysed under the action of acids but the risk in this case is that the flavanic structure may change and consequently the yield of the operation will be considerably reduced. As suitable acids, p-toluenesulphonic acid is preferred, it being possible to carry out the reaction, for example, in alcohols, in particular in methanol. According to the nature of the substituents to be hydrolysed the reaction may take from a few hours to several dozen hours and it may take place at the ambient temperature but may be accelerated by heating, optionally under reflux with the risk of partial decomposition of the desired products.

It is also possible to split the $OR_1$ groups by catalytic hydrogenation by means of molecular hydrogen or by the transfer of hydrogen in situ by means of a hydrogen donor such as cyclohexene. If the compound to be hydrogenated has a salt-forming group in the substituent in the 3-position, the free form or a salt of this group may be used.

The reaction may take place in the presence of a solvent such as: water, methanol, ethanol, isopropanol, tert.-butyl alcohol, ethyl acetate, dioxan or tetrahydrofuran. Hydrogenation may be effected at ambient temperature and under normal pressure but equally at an elevated temperature and/or under elevated pressure which reduces the duration of the reaction. The conditions of the reaction and the type of catalyst are preferably chosen in such a manner as to avoid breaking the flavanic heterocyclic nucleus and so as not to attack on the one hand the aromatic nuclei and on the other hand the desired substituents R. As suitable catalysts finely divided palladium or palladium on activated carbon have generally been satisfactory and the reaction is preferably effected at ambient temperature and under normal pressure.

Hydrogenatable groups of the radical R may at the same time be hydrogenated, especially if extremely reactive catalysts are used, such as palladium on carbon. However, it is possible to leave the group R intact by reducing the activity of these catalysts.

The compounds having a radical containing salt-forming groups, such as, for example, free carboxy groups, may, according to the conditions selected for the reaction, be obtained in the free form or in the form of salts, the said forms being mutually transformable one into another. The salts of compounds containing a free carboxy group are, for example, metal salts, in particular alkali metal salts, for example, sodium or potassium salts, and also alkaline-earth metal salts, for example, magnesium or calcium salts, or salts of ammonium, for example those with ammonia and organic bases as tri-lower alkylamines, for example, trimethylamine or triethylamine, in particular the non-toxic, pharmaceutically acceptable salts of the above type. They are obtained, for example, by treating the free compounds with metal hydroxides or carbonates, or with ammonia or amines, as well as with appropriate ion exchangers or organometallic compounds.

The compounds comprising basic groups may also be in the form of addition salts with acids, in particular in the form of non-toxic pharmaceutically acceptable salts, for example, with mineral acids, such as, hydrochloric acid, hydrobromic acid, sulphuric acid or phosphoric acid, or with organic carboxylic or sulphonic acids, for example aliphatic, cycloaliphatic, cycloaliphatic-aliphatic, aromatic, araliphatic, heterocyclic or heterocyclic-aliphatic acids, for example, acetic, propionic, succinic, glycolic, lactic, malic, tartaric, citric, ascorbic, maleic, phenylacetic, benzoic, 4-aminobenzoic, anthranilic, 4-hydroxybenzoic, salicylic, aminosalicylic, embonic or nicotinic acid, as well as methanesulphonic, ethanesulphonic, 2-hydroxyethanesulphonic, ethylenesulphonic, phenylsulphonic, p-methylphenylsulphonic, naphthalenesulphonic, sulphanilic or cyclohexylsulphamic acids. The salts of this type may be obtained, for example, by treating the free compounds containing basic groups with acids or with suitable anion exchangers.

The new compounds containing basic groups may be converted into their quaternary ammonium compounds by treatment with alkylating agents, such as lower alkyl halides, for example, methyl iodide, or lower alkyl sulphates or benzyl sulphates, such as dimethyl sulphate.

Some of the starting materials for the process described above are known but the majority are new. They may be prepared by a method known per se or more particularly by a new and advantageous method.

Thus, (+)-cyanidan-3-ol or one of the salts thereof may be reacted with a reactive ester of an alcohol of the formula

HO—R$_1$ in which R$_1$ has the meaning given above, and the radical R is introduced into the hydroxy group in the 3-position by etherification or esterification.

A reactive ester is especially an ester with a strong inorganic acid, especially with a hydrohalic acid, such as hydrochloric acid or hydrobromic acid or an organic sulphonic acid, preferably a lower alkanesulphonic acid, for example, methane- or ethane-sulphonic acid, or a benzenesulphonic acid optionally substituted in the benzene nucleus by methyl, chlorine or bromine, for example, p-toluenesulphonic acid or p-bromobenzenesulphonic acid.

By this process derivatives of (+)-cyanidan-3-ol are obtained, the 4 phenolic hydroxy groups of which are substituted. Of these tetra-ethers, (+)-3',4',5,7-O-tetrabenzyl-cyanidan-3-ol has already been the subject of a preparation according to a process limited strictly to the laboratory [K. Weinges and D. Seiler, Liebigs Ann. Chem. 714 193–204 (1968)] which recommends treating (+)-cyanidan-3-ol in solution in acetone with benzyl chloride in the presence of potassium iodide and potassium carbonate, the whole being carried out under nitrogen and under reflux for several hours. This is a conventional method of benzylation and, after processes of separation and crystallisation from ethanol, it results in a mixture of (+)-3',4',5,7-O-tetrabenzyl-8-benzyl-cyanidan-3-ol and (+)-3',4',5,7-O-tetrabenzyl-cyanidan-3-ol. The latter is finally isolated by column chromatography in a yield of 1 to 2% which is absurdly low and makes this method of obtaining (+)-3',4',5,7-O-tetrabenzyl-cyanidan-3-ol commercially unexploitable.

However, if benzyl chloride is replaced by another halide carefully chosen from among the radicals R$_1$ mentioned above, this method becomes perfectly acceptable, in particular with substituted or unsubstituted phenacyl chlorides and bromides, such as, for example, phenacyl chloride or phenacyl bromide or 4-bromophenacyl chloride or bromide or 4-phenylphenacyl chloride or bromide. After filtering the insoluble potassium carbonate and evaporating the acetone it is sufficient to take up the residue for crystallisation from an adequate solvent, such as, for example, a mixture of acetone and methanol. A good yield of the corresponding O-tetra-ether is obtained.

In addition, we have found that a new process, which is also a subject of the present invention, readily produces the intermediates in a very good yield. This process is characterised by the fact that the (+)-cyanidan-3-ol is reacted, in an aprotic organic solvent having an elevated dielectric constant, with an alkaline hydride or an alkaline carbonate and the tetra-alkaline salt of (+)-cyanidan-3-ol so obtained is reacted with a reactive ester of an alcohol of the formula

HO—R$_1$ using a ratio of (+)-cyanidan-3-ol to alkaline hydride to reactive ester of 1:approximately 4.25:approximately 4.5, or a ratio of (+)-cyanidan-3-ol to alkaline carbonate to reactive ester of 1:approximately 8:approximately 6.

The alkaline hydride is, in particular, sodium hydride which is used preferably in the form of a dispersion in an oil. The alkaline carbonate is preferably potassium carbonate.

The aprotic solvents having elevated dielectric constants are preferably amides, such as, for example, dimethylformamide, but may also be sulphoxides, such as, for example, dimethyl sulphoxide. However, dimethylformamide is the preferred solvent, firstly for economic reasons, since it can, in fact, be recovered by simple distillation under normal pressure, and secondly because it is simpler to use than dimethyl sulphoxide. In addition, it is important that the reaction medium should be as anhydrous as possible. Thus, by drying the dimethylformamide on a molecular sieve, then drying the solution of (+)-cyanidan-3-ol in dimethylformamide in the same manner, the formation of secondary products that are not desired is greatly inhibited without this drying operation impairing the formation of the desired products.

The reaction may take place in the presence of a quaternary ammonium salt such as tetra-n-butylammonium bisulphate which is used in a ratio of 0.1 to 0.5 mole per mole of (+)-cyanidan-3-ol, or of a crown ether, preferably 18-crown-6, which is used in a ratio of 0.5 mole per mole of (+)-cyanidan-3-ol.

The reaction is carried out at a temperature between approximately −25° C. and approximately +50° C. As it is known that dimethylformamide starts to decompose at as low as ambient temperature when it is in contact with basic substances, this decomposition is avoided as far as possible by effecting the reaction proper in this solvent at a temperature between about −25° C. and about +25° C., more particularly between about −5° C. and about 0° C. There is no danger of decomposition when dimethyl sulphoxide is used and the reaction may be carried out at a temperature lower than 50° C. and preferably between about +15° C. and about +30° C., for example, at ambient temperature.

According to the process of the invention, after the formation of the alkaline salt of (+)-cyanidan-3-ol, this salt does not remain stable in the dimethylformamide/sodium hydride medium even at a low temperature and it is therefore necessary to introduce immediately the etherification or esterification agent. If this is not done the chemical yield of the reaction will be reduced and there will be complications in the purification phase of the desired product. On the other hand, after adding the etherification or esterification agent the low temperature is still maintained for a certain period and the temperature is then allowed to rise slowly, for example to the ambient temperature. At this stage the reaction is terminated, the reaction liquor can be kept for more than 15 hours in this state without this changing the method of purification or impairing the quality of the desired product. It is also important to ensure efficient mixing of the reactive medium during the reaction.

The development of the reaction may be monitored by thin layer chromatography over silica gel using, for example, chloroform or dichloromethane as the mobile phase.

After eliminating the reation solvent by distillation the residue is taken up in an appropriate solvent which is used for the crystallisation of the intermediate. The proposed solvent for the crystallisation of the desired products is trichloroethylene which is particularly suitable. Other solvents, such as carbon tetrachloride, toluene and optionally ethyl acetate, ethanol, isopropanol or mixtures of solvents, such as, for example, carbon tetrachloride/n-hexane or acetone/methanol give good results. However, ethyl ether and n-hexane are less suitable and the same applies to acetone, pyridine, chloroform, dimethylformamide, dimethyl sulphoxide, tetrahydrofuran and dichloromethane in all of which the substances are soluble at ambient temperature.

The radical R is introduced by methods known per se into the intermediate obtained. Thus, for example, a halogen derivative of the formula hal—R can be made to react with these compounds. This reaction is carried out in the presence of a base, alkalis such as sodium or potassium hydroxide, silver oxide, sodium amide and sodium or potassium hydride being preferred. This etherification may be carried out in the presence of a non-reactive solvent, such as dioxan, tetrahydrofuran or toluene, or optionally in mixtures of these solvents with one another or with water. The reaction takes place at ambient temperature and it may be accelarated by heating, optionally to the boiling point of the solvent used. The duration of the reaction is between a few minutes and several days but a few hours generally suffice. When the base is soda or potash in aqueous solution and the intermediate is in a water-immiscible solvent a phase-transfer catalyst, such as tetrabutylammonium bisulphate, may be used.

If R is a hydroxyalkyl or an aminoalkyl radical it is also possible to obtain derivatives of the formula II by condensing an epoxide or an aziridine with the intermediates in an acid or basic medium.

If R is an aromatic radical the derivatives of the formula II may be obtained by reacting an aromatic halide with the intermediates. This reaction is carried out in an inert solvent, for example, tetrahydrofuran, optionally at ambient temperature, in the presence of a base, such as a tertiary amine, for example, trimethyl- or triethylamine, or in the presence of a fluoride, such as potassium fluoride or quaternary ammonium fluoride in the presence or absence of a crown ether, such as 18-crown-6. An alcoholate of the intermediates reacts, for example, with a halide of a heterocyclic compound. It is also possible to use an aromatic diester of phosphorous acid in the presence of catalytic quantities of a sulphonic acid, for example, p-toluenesulphonic acid.

The intermediates of the formula II in which R is hydrogen are added to olefins containing as substituents electron-attracting groups, such as cyano, nitro, ketone or ester groups in the presence of a base and the reagents may, for example, be dissolved in an inert water-immiscible solvent and the base may be a 50% aqueous sodium carbonate solution; a phase-transfer catalyst, such as benzyltrimethylammonium hydroxide, may then be used.

A derivative of an acid of the formula

HO—R such as an acid halide, acyl anhydride or acyl cyanide which may be formed in situ, is preferably used for the introduction of the radical R into the intermediates. A basic solvent, such as pyridine, is used in the presence or absence of a tertiary aliphatic amine, such as triethylamine, and/or pyridine, or a mixture of solvents at least one of which is basic, or an inert or basic solvent and a preferably alkaline catalyst. This reaction applies also to N-substituted isocyanates.

The esters of a mineral acid or a sulphonic acid with the intermediates may be obtained by reacting the latter with a halide of the said acid, or with a mineral polyacid still suitable for esterification in which one or two hydroxy groups respectively are substituted or blocked; the protective groups present are then eliminated by hydrolysis or hydrogenation, separately or together with the radicals $R_1$ protecting the aromatic hydroxy groups of the (+)-cyanidan-3-ol. These esters of mineral acids may also be obtained by the direct action of their anhydrides on the intermediates.

As a result of the close relationship between the new compounds in free form and in the form of their salts it is convenient, in the above and in the following, to understand references to the free compounds as also including the salts and, similarly, references to the salts as also including the free compounds.

The substituents R may be chirals and the new compounds may be in the form of pure stereoisomers or in the form of mixtures of stereoisomers. These latter may, on the basis of the physico-chemical differences between the constituents of the mixture, be resolved in known manner into the pure stereoisomers, for example, by means of chromatographic separation, for example, by thin layer chromatography or by any other suitable process of separation. The most active of the stereoisomers is preferably isolated.

The processes described above are put into practice according to methods known per se, in the absence or, preferably, in the presence of diluents or solvents, if necessary while cooling or heating, under elevated pressure and/or in an inert gaseous atmosphere, such as a nitrogen atmosphere.

The invention relates also to the methods of carrying out the process where a compound obtained as an intermediate product at any stage of the process is used as the starting material and the remaining stages of the said process are carried out or the latter is interrupted at any of its stages, or where a starting substance is formed under the conditions of the reaction or is used in the form of a reactive derivative. In this case, starting substances are preferably used which result, in accordance with the process, in compounds which are described above as being particularly valuable.

The pharmacologically acceptable compounds of the present invention may be used, for example, to obtain pharmaceutical preparations containing an effective quantity of the active substance in conjunction or in admixture with solid or liquid, mineral or organic carriers that can be used in pharmacy and that are suitable for enteral or parenteral administration. There are preferably used tablets or gelatine capsules containing the active substance in conjunction with diluents, for example lactose, dextrose, sucrose, mannitol, sorbitol, cellulose and/or glycine, and/or lubricants, for example, silica, talcum, stearic acid or the salts thereof, such as magnesium stearate or calcium stearate and/or polyethylene glycol; the tablets also contain binders, for example, magnesium silicate an aluminium silicate, starches, such as maize starch, wheat starch, rice starch or arrowroot, gelatine, gum tragacanth, methylcellulose, sodium carboxymethylcellulose and/or polyvinylpyrrolidone and, if desired, dissociation agents, for example, starches, galactan, alginic acid or a salt thereof, such as sodium alginate, and/or effervescent mixtures or adsorption agents, colorants, taste correctives and sweeteners. The injectable preparations are preferably aqueous isotonic solutions or suspensions and the suppositories are especially emulsions or suspensions in oil. The pharmaceutical preparations may be sterilised and/or contain auxiliaries, such as preservatives, stabilising agents, wetting agents and/or emulsifiers, solubilisers, salts serving to regulate the osmotic pressure, and/or buffers. The present pharmaceutical preparations, which may, if desired, contain other pharmacologically valuable substances, are prepared in a manner known per se, for example, by means of conventional mixing, granulating or dragée-making processes and they contain of the order of approximately 0.1% to 75%, in particular of the order of approximately 1% to 50%, of the active substance.

The substances according to the present invention are administered in a dose of 1 to 1000 mg and preferably 1 to 500 mg per unit dosage.

The invention relates also to the new intermediates of the formula II in which $OR_1$ and OR have the meanings given above, except for the compound in which all the radicals $R_1$ are benzyl and R is hydrogen or methyl.

The invention relates also to the new starting materials of the formula II in which $OR_1$ has the meaning given above and OR is a free hydroxy group.

The invention is described in more detail in the non-limiting examples which follow, in which the temperatures are given in degrees Centigrade.

EXAMPLE 1

In a 3 liter spherical flask, a suspension of 12 g of palladium chloride ($PdCl_2$) in 1800 ml of methanol is hydrogenated for 2 hours at ambient temperature; 2400 ml of hydrogen are used. The methanol is decanted off and the palladium black formed is washed 4 times with 800 ml of fresh methanol which eliminates the hydrochloric acid formed as well as the traces of soluble $PdCl_2$ that have not reacted. The methanol is then substituted by ethyl acetate by 3 successive washes with 500 ml of ethyl acetate. After the last washing, a thin layer of ethyl acetate is left on the palladium black to prevent spontaneous ignition thereof on contact with air.

A solution of 40 g of (+) 3',4',5,7-O-tetrabenzyl-3-O-methyl-cyanidan-3-ol in 1600 ml of ethyl acetate is added to this freshly prepared suspension of palladium black and the mixture is hydrogenated for 3 hours; the hydrogen consumption is 6600 ml. The palladium is then removed by filtration and the filtrate is evaporated to dryness under a medium vacuum at 40° C. The residue is taken up in 2000 ml of water and the water evaporated under a medium vacuum at 40° C. until a volume of approximately 100 ml is reached. This operation, which removes azeotropically the ethyl acetate and the toluene formed by removal of the benzyl groups, is repeated three times and the final volume of 100 ml is dried by lyophilisation. The yield is quantitative, consisting of 18.5 g of (+) 3-O-methyl-cyanidan-3-ol. Mp.: 118°-120°; $[\alpha]_{29}^D = +2.76$ in EtOH (c=0.5).

EXAMPLE 2

A suspension of 6.0 g of palladium chloride in 900 ml of methanol is hydrogenated in a 2000 ml spherical flask for 1½ hours at ambient temperature; 1100 ml of hydrogen are consumed. After decanting the methanol the mixture is washed 3 times with 200 ml of methanol then 3 times with 200 ml of ethyl acetate.

A solution of 21.2 g of (+) 3',4',5,7-O-tetrabenzyl-3-O-butyl-cyanidan-3-ol in 900 ml of ethyl acetate is then added and the mixture is hydrogenated for 5 hours at ambient temperature; the hydrogen consumption is 3250 ml. The palladium is removed by filtration and the filtrate is evaporated in a medium vacuum at 40° C. The residue is taken up in 500 ml of water and then evaporation to a volume of 50 ml is carried out. This operation is repeated 4 times to remove azeotropically the ethyl acetate and the toluene formed during the hydrogenation. After the last evaporation step the residue is finally dried under 10 mm Hg at 60° C. to constant weight. The yield of (+) 3-O-butyl-cyanidan-3-ol obtained is quantitative, amounting to 10.4 g. Mp.: 103°-104° C.

EXAMPLE 3

The procedure is as in Example 2 except that 21.6 g of (+) 3',4',5,7-O-tetrabenzyl-3-O-butyrylcyanidan-3-ol are used.

After the residue has been dried to constant weight as in Example 2, it is dissolved in a mixture of 5500 ml of water and 1100 ml of ethanol at ambient temperature, then filtered on a fluted filter and the filtrate is concentrated in a medium vacuum at 40° to a volume of 2500 ml; the result is a paste-like oil. The solution is decanted off and left at 4° for 3 days; the white precipitate which forms is filtered off, washed with cold water and dried under 10 mm Hg over $P_2O_5$ at 50° C. to constant weight. The yield of (+) 3-O-butyryl-cyanidan-3-ol is 7.3 g, that is 67.6%. Mp.: 112°-113° C.

EXAMPLE 4

The procedure is as in Example 2 except that 22.5 g of (+) 3',4',5,7-O-tetrabenzyl-3-O-(3,3-dimethylbutanoyl)-cyanidan-3-ol are used. The yield of (+) 3-O-(3,3-dimethylbutanoyl)-cyanidan-3-ol is quantitative, amounting to 11.6 g. Mp.: 118°-120° C.

EXAMPLE 5

The procedure is as in Example 2 except that 22 g of (+) 3',4',5,7-O-tetrabenzyl-3-O-(3 carboxypropionyl)-cyanidan-3-ol are used.

After the ethyl acetate and the toluene have been removed azeotropically with water, the residue is dissolved in 1000 ml of water, evaporated until it becomes slightly turbid (approximately 500 ml), filtered and the filtrate lyophilised to constant weight. The yield of (+) 3-O-(3-carboxypropionyl)-cyanidan-3-ol is practically quantitative, amounting to approximately 11.7 g. Mp.: 102°-106° C.

EXAMPLE 6

The procedure is as in Example 1, except that 50 g of (+) 3',4',5,7-O-tetrabenzyl-3-O-decanoylcyanidan-3-ol are used.

After the ethyl acetate has been evaporated, the residue is dried in vacuo at 40° C. and dissolved in 300 ml of ethanol; the solution is evaporated to 50 ml and 250 ml of ethanol and 250 ml of water are added. This solution is evaporated to 50 ml, 500 ml of water are added and the solvent is driven off under a medium vacuum at 40° C. The residue is dried to constant weight under a high vacuum over $P_2O_5$. The yield of (+) 3-O-decanoyl-cyanidan-3-ol is 26 g, that is, 94.3%. Mp.: 71°-74° C.

EXAMPLE 7

26.6 g of (+) 3',4',5,7-O-tetrabenzyl-3-O-palmitoyl-cyanidan-3-ol are dissolved in 900 ml of ethyl acetate (dissolution is accelerated by heating) in a 2000 ml spherical flask. 16.0 g of 10% palladium on activated carbon are added and the mixture is hydrogenated. The palladium and the activated carbon are removed by filtration and then the filtrate is evaporated to dryness. The residue is a caked mass which is taken up in 400 ml of hot methanol. 1500 ml of water are added to the methanol solution while stirring and stirring is continued overnight at ambient temperature, then for 48 hours on an ice bath. The precipitate formed is isolated by filtration and dried under a high vacuum over $P_2O_5$ at ambient temperature. The yield of (+) 3-O-palmitoyl-cyanidan-3-ol is 12.4 g, that is, 78.2%. Mp: 67°–69° C.

EXAMPLE 8

The procedure is as in Example 2: the palladium black is prepared by hydrogenation of a suspension of 18 g of palladium chloride in 900 ml of ethyl acetate, then 40 g of a solution of (+) 3',4',5,7-O-tetrabenzyl-3-O-tetrahydrophthalyl-cyanidan-3-ol in 1800 ml of ethyl acetate are hydrogenated as in Example 1. After the organic solvents (ethyl acetate and toluene) have been removed azeotropically with water, the final residue is dried to constant weight at ambient temperature under a high vacuum over $P_2O_5$. The yield of (+) 3-O-(2-carboxycyclohexanecarbonyl)-cyanidan-3-ol is 22.2 g, that is, a quantitative yield. Mp.: 138°–140° C.

EXAMPLE 9

A suspension of 30 g of palladium chloride in 4.5 liters of methanol is hydrogenated in a 10 liter spherical flask. The reaction lasts for 1 hour and consumes 4.92 liters of hydrogen. The palladium black formed is washed, first of all 4 times with 1 liter of methanol, then 4 times with 1 liter of ethyl acetate. A solution of 113 g of (+) 3',4',5,7-O-tetrabenzyl-3-O-benzoyl-cyanidan-3-ol in 4 liters of ethyl acetate is added to the catalyst impregnated with ethyl acetate and the mixture is hydrogenated for approximately 1½ hours. The Pd catalyst is isolated by filtration, washed on the filter with 250 ml of ethyl acetate and the fractions of ethyl acetate are recombined and distilled under a medium vacuum at 40° C. The residue is taken up in 5 liters of water, the suspension obtained is agitated for 30 minutes at ambient temperature then the water is driven off under a medium vacuum at 40° C. to a volume of approximately 500 ml. This operation is repeated twice more and the suspension is finally evaporated to dryness; the residue is dried to constant weight over silica gel under a high vacuum. The yield of (+) 3-O-benzoyl-cyanidan-3-ol is quantitative, consisting of 59 g. Mp.: 132°–135° (amorphous product).

EXAMPLE 10

The procedure is as in Example 9 except that 115.8 g of (+) 3',4',5,7-O-tetrabenzyl-3-O-(4-fluorobenzoyl)-cyanidan-3-ol are used. The yield is 61.5 g of (+) 3-O-(4-fluorobenzoyl)-cyanidan-3-ol, that is, 99.5%. Mp.: 131°–133° C.

EXAMPLE 11

As in Example 9, the palladium black is prepared from a suspension of 40 g palladium chloride in 4.5 liters of methanol, the methanol is subtituted by ethyl acetate and a solution of 130 g of (+) 3',4',5,7-O-tetrabenzyl-3-O-(3,4-dibenzyloxybenzoyl)-cyanidan-3-ol in 5.5 liters of ethyl acetate is hydrogenated. After the organic solvents (ethyl acetate and toluene) have been removed azeotropically with water, the residue is dissolved in 500 ml of water and this solution is lyophilised to constant weight. The yield of (+) 3-O-protocatechyl-cyanidan-3-ol is quantitative, amounting to 57.5 g. Mp.: 166°–168° C.

EXAMPLE 12

The procedure is as in Example 2 except that 24.5 g of (+) 3',4',5,7-O-tetrabenzyl-3-O-(acetylsalicylyl)-cyanidan-3-ol are used. The yield of (+) 3-O-(acetylsalicylyl)-cyanidan-3-ol is quantitative, amounting to 13.5 g. Mp.: 118°–119° C.

EXAMPLE 13

The procedure is as in Example 1: the palladium black is prepared from 24 g of palladium chloride in 3.6 liters of methanol, then 64 g of (+) 3',4',5,7-O-tetrabenzyl-3-O-(2-carboxybenzoyl)-cyanidan-3-ol in 3.5 liters of ethyl acetate are hydrogenated. After the catalyst has been filtered off and the solvents (ethyl acetate and toluene) evaporated, the residue is dissolved in 2 liters of ethanol, the solution is evaporated to approximately 100 ml, this operation is repeated twice then the residue is dried under a high vacuum at 40° C. to constant weight. The yield of (+) 3-O-(2-carboxybenzoyl)-cyanidan-3-ol is quantitative, amounting to 35 g. Mp.: 139°–142° C.

EXAMPLE 14

The palladium black is prepared as in Example 1, then the methanol is substituted by ethyl acetate and 30.8 g of (+) 3',4',5,7-O-tetrabenzyl-3-O-(N-phenylcarbamoyl)-cyanidan-3-ol in 1600 ml of ethyl acetate are hydrogenated. After filtration of the catalyst, the ethyl acetate is then evaporated to a volume of approximately 50 ml, 250 ml of water are added and the pH is adjusted to 6 by means of an aqueous solution of 1N NaOH. Evaporation to dryness in vacuo is carried out at 40° C. then 500 ml of water are added and evaporated three times, the residue is dissolved in 1 liter of ethanol which is distilled and this operation is repeated. The product is taken up in a mixture of 300 ml of ethanol and 300 ml of water, evaporated, finally taken up in 500 ml of water and evaporated to 100 ml. The precipitate formed is filtered and dried to constant weight at 40° C. in vacuo. The yield of (+) 3-O-(N-phenylcarbamoyl)-cyanidan-3-ol is 15.0 g, that is, 91.6%. Mp.: 189°–200° C.

EXAMPLE 15

The procedure is as in Example 2 except that 18.2 g of (+) 3',4',5,7-O-tetrabenzyl-3-O-methanesulphonyl-cyanidan-3-ol are used and hydrogenation is carried out in 600 ml of ethyl acetate. The solvents are distilled off at ambient temperature and the residue is dried at ambient temperature under a high vacuum. The residue is taken up in 500 ml of ethanol at ambient temperature and distillation to approximately 50 ml is carried out under a high vacuum at 0° C.; this operation is repeated twice, then the product is finally dried at 35° C. for 15 minutes in vacuo, and the residue is dried to constant weight under a high vacuum at ambient temperature. The yield of (+) 3-O-methanesulphonyl-cyanidan-3-ol is quantitative, amounting to 9.2 g. The substance decomposes slowly even at ambient temperature; it is preserved for several days in a freezer at −30° C.

EXAMPLE 16

As in Example 7, a solution of 40 g of (+) 3',4',5,7-O-tetrabenzyl-3-O-(4-methylbenzenesulphonyl)-cyanidan-3-ol in 1.8 liters of ethyl acetate are hydrogenated in a 3000 ml spherical flask over 20 g of 10% palladium on activated carbon. The hydrogenation takes 2½ hours. The palladium and the carbon are filtered off, the filtrate is evaporated to dryness in vacuo at ambient temperature and 1.7 liters of ethanol are added and distilled at 0° C. under a high vacuum. When the volume has been brought to approximately 100 ml, 800 ml of ethanol are added and distilled at 0° C. under a high vacuum. The residue is then heated at 35° C. for 15 minutes under a high vacuum and maintained at ambient temperature under a high vacuum until a constant weight is reached. The yield of (+) 3-O-(4-methylbenzenesulphonyl)-cyanidan-3-ol is quantitative, amounting to 22 g.

The product is preserved in a freezer at −30° C. to avoid decomposition.

EXAMPLE 17

A suspension of 29 g of palladium chloride in 2.9 liters of methanol are hydrogenated in a 10 liter spherical flask. The methanol, charged with hydrochloric acid, is decanted off and the palladium black formed is washed first of all three times with 300 ml of methanol then three times with 300 ml of ethyl acetate. A solution of 54.5 g of (+) 3',4',5,7-O-tetrabenzyl-3-O-(2-cyanoethyl)-cyanidan-3-ol in 2.9 liters of ethyl acetate are then introduced onto the palladium black and the mixture is hydrogenated. After the catalyst has been removed by filtration, the solvent is evaporated in a medium vacuum, the residue is dissolved in 1.5 liters of water and the mixture is evaporated in a rotary evaporator (Rotovapor) at 40° C. under a medium vacuum to 500 ml. This operation is repeated a further twice and the last fraction of 500 ml is lyophilised to constant weight. The (+) 3-O-(2-cyanoethyl)-cyanidan-3-ol is obtained in a yield of 25 g, that is, 94%.

EXAMPLE 18

56 g of (+) 3',4',5,7-O-tetrabenzyl-3-O-(2-cyanoethyl)-cyanidan-3-ol, 4 liters of absolute ethanol and 100 ml of chloroform are placed in a 10 liter spherical flask. With the exclusion of moisture the mixture is heated at 60° C. until complete dissolution occurs, then the solution is left to cool to ambient temperature and argon is bubbled through the solution. Still under argon, 25 g of 10% palladium on activated carbon are added and hydrogenation is carried out. 12 liters of hydrogen are consumed. The hydrogen is then substituted by nitrogen, the catalyst filtered off and the filtrate evaporated to dryness in a medium vacuum. The residue is mixed with 1 liter of ethyl acetate and the resulting suspension is agitated for 30 minutes at 40° C. The solvent is evaporated to a volume of approximately 200 ml, the mixture is cooled to approximately 0° C., filtered and the precipitate washed with ethyl acetate. The treatment with ethyl acetate is repeated twice. Finally the precipitate is washed twice with ethyl acetate then twice with methylene chloride before being dried under a high vacuum for 24 hours at ambient temperature. The product is dissolved in 2 liters of water, the solution is brought to 200 ml by distilling under a medium pressure and 1.8 liters of water are added and evaporated in the same manner to 200 ml. This final solution is lyophilised to constant weight of the residue. The chlorohydrate of (+) 3-O-(3-aminopropyl)-cyanidan-3-ol is obtained in a yield of 21 g, that is, 68.4%. Mp. (with decomposition): 195° C.

EXAMPLE 19

An approximately 55% dispersion of 5.0 g of sodium hydride in oil is introduced into a 500 ml spherical flask provided with a reflux condenser closed with a calcium chloride tube, a dropping funnel with a pressure equaliser, a nozzle for the introduction of nitrogen, a thermometer and an agitation mechanism. A strong current of nitrogen is passed through for 5 minutes then the supply of nitrogen is reduced so that 60 ml of anhydrous tetrahydrofuran can be introduced dropwise through the dropping funnel. The mixture is heated to 40° C. by means of an external oil bath and while stirring 7.5 ml (17 g) of freshly distilled methyl iodide are introduced dropwise. Then a solution of 52.0 g of (+) 3',4',5,7-O-tetrabenzyl-cyanidan-3-ol in 170 ml of anhydrous tetrahydrofuran is added dropwise over the course of one hour. The mixture is allowed to react for 1½ hours while stirring and maintaining the temperature at 40° C. The mixture is then brought to ambient temperature, 200 ml of water are added and the mixture is stirred for 15 minutes. The reaction mixture is filtered on a fluted filter and the filtrate is placed in a separating funnel containing 200 ml of toluene and 200 ml of water. The organic phase is separated and washed with 50 ml of water whilst the aqueous phase is extracted twice with 400 ml of methylene chloride. All the organic fractions are recombined, dried over MgSO$_4$ and evaporated under a medium vacuum at 40° C. The residue is dried overnight under 15 mm Hg at 45° C.; it weighs 51 g.

This dry residue is dissolved at 100° C. in 510 ml of methoxyethanol, filtered hot, and the filtrate is allowed to cool slowly while stirring. After 8 hours the precipitate that has formed is filtered off, washed with 30 ml of cold methoxyethanol and dried in vacuo at 50° C. overnight. The yield of (+) 3',4',5,7-O-tetrabenzyl-3-O-methyl-cyanidan-3-ol is 45.5 g, that is, 85.5%. Mp: 124°–125° C.

EXAMPLE 20

1.5 liters of a 50% aqueous solution of NaOH, a solution of 52 g of (+) 3',4',5,7-O-tetrabenzylcyanidan-3-ol in 1.5 liters of butyl chloride and 6.8 g of tetrabutylammonium hydrogen sulphate are introduced into a 6 liter spherical flask provided with a mechanical agitator and a reflux condenser. The mixture is heated to 50° C. and this temperature is maintained for 2 hours 45 minutes while stirring vigorously. After cooling to ambient temperature the two phases are separated, the organic phase is washed three times with 300 ml of water and dried over MgSO$_4$. After filtration the butyl chloride is distilled and is recovered. The residue is recrystallised twice in 3.2 liters of absolute ethanol. After drying, (+) 3',4',5,7-O-tetrabenzyl-3-O-butyl-cyanidan-3-ol is obtained in a yield of 40.0 g, that is, 70.8%. Mp.: 55°–56° C.

EXAMPLE 21

A solution of 52 g of (+) 3',4',5,7-O-tetrabenzyl-cyanidan-3-ol in 360 ml of anhydrous pyridine is introduced into a 500 ml 4-necked spherical flask fitted with a dropping funnel with pressure equaliser, a condenser closed with a calcium chloride tube, a nozzle for the introduction of nitrogen and a magnetic agitator; 17 g of butyryl chloride are then added under nitrogen and while agitating. The mixture is allowed to react at ambient temperature while stirring for 5 hours 30 minutes, then poured into 500 ml of water containing pieces of ice. The mixture is mixed for 1 hour and the oily layer formed is separated. The oily layer is mixed first of all with 500 ml of an aqueous solution of 1N NaHCO₃ then twice with 500 ml of water; a solid product is formed which is filtered off, washed with water and dried in vacuo. Recrystallisation is carried out in a mixture of 3 liters of ethanol and 400 ml of acetone. After drying, (+) 3',4',5,7-O-tetrabenzyl-3-O-butyryl-cyanidan-3-ol is obtained in a yield of 52.4 g, that is, 91%. Mp.: 92°–93° C.

EXAMPLE 22

The procedure is as in Example 21, but using 21.5 g of 3,3-dimethylbutanoyl chloride. The duration of the reaction is 1 hour. After washing with water 56 g of the crude product is obtained; this is dissolved in 400 ml of acetone and 3 liters of ethanol are added dropwise to this solution which is left to crystallise for 6 days. (+) 3',4',5,7-O-tetrabenzyl-3-O-(3,3-dimethylbutanoyl)-cyanidan-3-ol is obtained in a yield of 50.6 g, that is, 84.6%. Mp.: 58° C.

EXAMPLE 23

52 g of (+) 3',4',5,7-O-tetrabenzyl-cyanidan-3-ol, 400 ml of triethylamine, 80 ml of pyridine and 16 g of succinic anhydride are introduced into a 1 liter spherical flask fitted with a reflux condenser closed with a calcium chloride tube. The mixture is refluxed for 1 hour, then the solvents are removed under a medium vacuum at 40° C. The residue is washed twice with 300 ml of water acidified to a pH of 3 with HCl, then twice with distilled water. Recrystallisation is carried out twice in 3 liters of ethanol. (+) 3',4',5,7-O-tetrabenzyl-3-O-(3-carboxypropionyl)-cyanidan-3-ol is obtained in a yield of 47.3 g, that is, 81.8%. Mp.: 95°–96° C.

EXAMPLE 24

The procedure is as in Example 21 except that in a 1 liter spherical flask 104 g of (+) 3',4',5,7-O-tetrabenzyl-cyanidan-3-ol in 720 ml of pyridine and in the presence of 61 g of capric chloride are used. The mixture is heated at 50° C. for 1½ hours while stirring then poured into 3 liters of a mixture of water and crushed ice, mixed for 1 hour, and the precipitate formed filtered, washed first of all twice with a 1 liter aqueous solution of 1N NaHCO₃, then twice with 1 liter of water and dried in vacuo at ambient temperature over P₂O₅. Finally the mixture is recrystallised in 1.4 liters of methoxyethanol. (+) 3',4',5,7-O-tetrabenzyl-3-O-decanoyl-cyanidan-3-ol is obtained in a yield of 121.7 g, that is, 94.5%. Mp.: 88°–89° C.

EXAMPLE 25

The procedure is as in Example 21 using 44 g of palmitoyl chloride and heating the reaction medium at 90° C. for 2 hours. The resulting (+) 3',4',5,7-O-tetrabenzyl-3-O-palmitoyl-cyanidan-3-ol is purified by dissolving under heat in 80 ml of acetone and 3 liters of ethanol are added dropwise to this solution. The yield of the desired substance is 68.4 g, that is, 96.2%. Mp.: 57°–59° C.

EXAMPLE 26

The procedure is as in Example 23 but using 24.5 g of tetrahydrophthalic anhydride. The reaction mixture is refluxed for 45 minutes, the solvent is removed by distillation under a medium vacuum at 40° C. and the residue, dissolved in 600 ml of methylene chloride, is extracted twice with 500 ml of 2N HCl and twice with 500 ml of distilled water. The solution of methylene chloride is dried over MgSO₄ then the solvent is evaporated off. The residue is recrystallised in a mixture of carbon tetrachloride and petroleum ether. (+) 3',4',5,7-O-tetrabenzyl-3-O-tetrahydrophthalyl-cyanidan-3-ol is thus obtained in a yield of 55.2 g, that is, 86%. Mp.: 67°–68° C.

EXAMPLE 27

The procedure is as in Example 21, except that 22.5 g of benzoyl chloride are used and the reaction mixture is heated at 80° C. for 6 hours. The solidified product obtained after washing with NaHCO₃ and water is recrystallised in a mixture of 7 liters of ethanol and 1.25 liters of acetone. (+) 3',4',5,7-O-tetrabenyl-3-O-benzoyl-cyanidan-3-ol is obtained in a yield of 50.1 g, that is, 83%. Mp.: 115°–116° C.

EXAMPLE 28

The procedure is as in Example 21 except that 25.4 g of 4-fluorobenzoyl chloride are used and the reaction mixture is maintained at ambient temperature for 7 hours. The solidified product is finally dissolved in 3.5 liters of acetone while heating and precipitated by adding 800 ml of water. By cooling, (+) 3',4',5,7-O-tetrabenzyl-3-O-(4-fluorobenzoyl)-cyanidan-3-ol is finally obtained in a yield of 52.2 g, that is, 84.4%. Mp.: 154° C.

EXAMPLE 29

The procedure is as in Example 21 except that a solution of 56.5 g of 3,4-dibenzyloxybenzoyl chloride in 130 ml of pyridine is added. The reaction mixture is stirred at ambient temperature for 2 hours 45 minutes. The final solidified product is recrystallised twice from acetone. (+) 3',4',5,7-O-tetrabenzyl-3-O-(3,4-dibenzyloxybenzoyl)-cyanidan-3-ol is obtained in a yield of 56.5 g, that is, 73%. Mp.: 162°–163° C.

EXAMPLE 30

The procedure is as in Example 21, except that a solution of 32 g of acetylsalicylyl chloride in 180 ml of pyridine is added and the reaction mixture is stirred for 2 hours at 65° C. After washing with NaHCO₃ and water, the solidified crude product is recrystallised first from 8 liters of ethanol, then from a mixture of 5 liters of ethanol and 1.2 liters of acetone. The yield of (+) 3',4',5,7-O-tetrabenzyl-3-O-(acetylsalicylyl)-cyanidan-3-ol is 44.8 g, that is, 69%. Mp.: 136°–137° C.

EXAMPLE 31

260 g of (+) 3',4',5,7-O-tetrabenzyl-cyanidan-3-ol, 89 g of phthalic anhydride, 3 liters of triethylamine and 1 liter of pyridine are introduced into a 4-necked 6 liter spherical flask fitted with a mechanical stirrer, a reflux condenser closed with a calcium chloride tube, a nozzle for the introduction of nitrogen and a thermometer. Under nitrogen, the mixture is refluxed (92° C.) for 9 hours then allowed to cool to ambient temperature and filtered on a fluted filter. The mixture is evaporated to dryness in a medium vacuum at 40° C. in a rotary evaporator (Rotovapor) and the oily residue is dissolved in 500 ml of methylene chloride and extracted twice with 500 ml of aqueous 2N HCl then twice with 500 ml of water. The organic solution is dried over MgSO₄, filtered and evaporated to dryness. The crude residue is recrystallised from 2.5 liters of toluene and 1.6 liters of ligroin. The crystallised product is dried to constant weight under a high vacuum at ambient temperature. The yield of (+) 3′,4′,5,7-O-tetrabenzyl-3-O-(2-carboxybenzoyl)-cyanidan-3-ol is 221.6 g, that is, 69.4%. Mp.: 127°–129° C.

EXAMPLE 32

The procedure is as in Example 21 except that a 1 liter spherical flask and 65 g of (+) 3′,4′,5,7-O-tetrabenzyl-cyanidan-3-ol in 800 ml of pyridine are used. The mixture is heated to 100° C. under nitrogen and 17.1 ml (18.7 g) of N-phenylisocyanate are added dropwise. The mixture is left for 1 hour at 100° C., allowed to cool to ambient temperature, filtered on a fluted filter and 6 liters of water are added while stirring vigorously; a white precipitate is formed. The precipitate is filtered off, washed with 6 liters of water and dried under a medium vacuum at 60° C. for 2 days. It is recrystallised from 8 liters of acetone which produces 60.7 g, then, after concentrating to approximately 2 liters, a further 16.2 g is recovered. The yield of (+) 3′,4′,5,7-O-tetrabenzyl-3-O-(N-phenylcarbamoyl)-cyanidan-3-ol is thus 76.9 g, that is, 100%. Mp.: 204° C.

EXAMPLE 33

A solution of 65 g of (+) 3′,4′,5,7-O-tetrabenzyl-cyanidan-3-ol in 500 ml of pyridine and 25 ml of triethylamine is introduced into a 3-necked 750 ml spherical flask fitted with a magnetic agitator, a calcium chloride tube, a separating funnel and a nozzle for the introduction of nitrogen. A current of nitrogen is passed through and the mixture is cooled to −15° C., then 23 g of methanesulphonyl chloride are added dropwise in the course of 30 minutes. The reaction mixture is agitated for 30 minutes at −15° C., then poured into 2.5 liters of a mixture of water and crushed ice. The precipitate formed is filtered off and mixed with 1 liter of water, then filtered and dried in vacuo over P$_2$O$_5$. The product is recrystallised from 2 liters of n-butanol, filtered, washed with 250 ml of methanol then again with 500 ml of methanol. The substance is dried in vacuo over P$_2$O$_5$ at ambient temperature. The yield of (+) 3′,4′,5,7-O-tetrabenzyl-3-O-methanesulphonyl-cyanidan-3-ol is 60.5 g, that is, 83%. Mp.: 138°–139° C.

EXAMPLE 34

158 g of (+) 3′,4′,5,7-O-tetrabenzyl-cyanidan-3-ol and 250 ml of pyridine are introduced into a 4-necked 500 ml spherical flask fitted with a reflux condenser closed with a calcium chloride tube, a nozzle for the introduction of nitrogen, a dipping thermometer and a magnetic agitator. The mixture is heated to 90° C. and the (+) 3′,4′,5,7-O-tetrabenzyl-cyanidan-3-ol passes into solution. 67 g of 4-methylbenzenesulphonyl chloride are then added while heating and the solution is maintained at 90° C. under nitrogen, while stirring, for 4 hours. The reaction liquor is then cooled to −30° C. for 2½ hours; a precipitate is formed. 1.5 liters of water are added, the mixture is mixed and the precipitate is filtered off and washed with aqueous 1N NaHCO$_3$, then with water until the filtrate is neutral. The substance is recrystallised from 5 liters of chloroform and 20 liters of isopropanol. The yield of (+) 3′,4′,5,7-O-tetrabenzyl-3-O-(4-methylbenzenesulphonyl)-cyanidan-3-ol is 162.9 g, that is, 84.3%. Mp.: 173°–174° C.

EXAMPLE 35

First of all a solution of 300 g of (+) 3′,4′,5,7-O-tetrabenzyl-cyanidan-3-ol in 3 liters of toluene then 4.5 liters of a 50% aqueous solution of NaOH and finally 16 g of Triton B are introduced in succession, while stirring, into a 20 liter spherical flask fitted with a separating funnel and a mechanical agitator. Whilst maintaining the agitation, 82 g of acrylonitrile are added dropwise over the course of 45 minutes. The mixture is stirred vigorously for 2 hours at ambient temperature, 30 g of acrylonitrile are added and stirring is maintained overnight. A third portion of 100 g of acrylonitrile is introduced into the reaction medium. Stirring is maintained for a further 2 hours then the toluene phase is isolated and washed three times with 1 liter of 0.1N HCl then with 2 liters of water. The toluene phase is then dried over MgSO$_4$ and the toluene is evaporated. The residue is taken up in 1.8 liters of acetone and the acetone solution is poured, while stirring, into 5.4 liters of boiling ethanol. The (+) 3′,4′,5,7-O-tetrabenzyl-3-O-(2-cyanoethyl)-cyanidan-3-ol is separated by cooling. It is filtered and dried. Yield: 318 g, that is, 98%. Mp.: 100°–101° C.

EXAMPLE 36

A three-necked 500 ml spherical flask is fitted with a nozzle for the introduction of nitrogen, a dropping funnel with pressure equaliser, a calcium chloride tube and a magnetic stirrer. 52 g of (+) 3′,4′,5,7-O-tetrabenzyl-cyanidan-3-ol, 260 ml of anhydrous dioxan and 130 mg of p-toluenesulphonic acid are introduced into this flask. 26 ml (24 g) of dihydropyran are added dropwise while stirring. Stirring is continued at ambient temperature for 2½ hours, then the mixture is filtered and the filtrate evaporated to dryness under a medium vacuum. The residue is dissolved in 500 ml of chloroform, this solution is washed twice with 300 ml of aqueous 1N NaHCO$_3$, then with 300 l ml of distilled water. The chloroform solution is dried over MgSO$_4$, filtered and evaporated. The residue is dried under a high vacuum at ambient temperature. (+) 3′,4′,5,7-O-tetrabenzyl-3-O-tetrahydropyranyl-cyanidan-3-ol is obtained in the form of a mixture of the two diastereoisomers in a yield of 56 g, that is, 95.3%.

The product is yielded in the form of a caked mass for which it is not possible to determine a melting point.

EXAMPLE 37

A suspension in 1 liter of freshly distilled dimethylformamide of 9.28 g of a 55% dispersion of sodium hydride in oil (51 g of NaH) is prepared under nitrogen whilst stirring vigorously. This suspension is brought to a temperature of between −5° and 0° C. by means of an external cooling bath.

A solution of 145 g of (+)-cyanidan-3-ol in 2 liters of freshly distilled dimethylformamide are added to this cooled suspension in such a manner that the temperature of the suspension remains between −5° and 0° C. (duration of the introduction: approximately 1 hour). Hydrogen is evolved and removed with the nitrogen circulation.

When the introduction of (+)-cyanidan-3-ol is complete, the reaction is allowed to proceed at low temperature for 15 minutes, in the course of which the evolution of hydrogen gas is practically complete. Then, over the course of approximately 1½ hours, 267.5 ml, that is, 385 g, of benzyl bromide are introduced in such a manner that the temperature of the reaction medium is maintained between −5° and 0° C. This temperature is maintained for a further 30 minutes after the introduction of the benzyl bromide, then the temperature is allowed to rise slowly to ambient temperature.

The dimethylformamide is recovered by distillation in vacuo at 60° C. and the oily residue is taken up in 3 liters of trichloroethylene. This organic solution is washed three times with 3 liters of distilled water then is filtered to remove impurities in the suspension.

By concentrating and cooling to 5° C. several times in succession, 159 g of practically pure (+) 3',4',5,7-O-tetrabenzyl-cyanidan-3-ol are crystallised. Yield: 51%. The product is in the form of white needles. Mp: 144°–145° C.

EXAMPLE 38

The process is carried out under the same conditions as in Example 37 except that dimethylformamide previously dried on a molecular sieve (4 Å, 2 mm) is used and the solution of (+)-cyanidan-3-ol in the dimethylformamide is dried on a molecular sieve (4 Å, 2 mm). (+) 3',4',5,7-O-tetrabenzyl-cyanidan-3-ol is obtained in a yield of 55%.

EXAMPLE 39

The procedure is as in Example 37 but the benzyl bromide is replaced by 2.25 moles of benzyl chloride. After the reaction medium has been allowed to attain ambient temperature, this temperature is maintained for 10 hours while stirring, before distilling off the dimethylformamide. The yield of (+) 3',4',5,7-O-tetrabenzyl-cyanidan-3-ol is 57%.

EXAMPLE 40

A solution of 1.45 g of (+)-cyanidan-3-ol in 20 ml of freshly distilled dimethyl sulphoxide is added slowly, while stirring and at ambient temperature, to a suspension in 10 ml of freshly distilled dimethyl sulphoxide, maintained under nitrogen, of 0.93 g of a 55% dispersion of sodium hydride in oil (0.51 g of NaH). Hydrogen is evolved and removed by the nitrogen circulation. After stirring for 1 hour at ambient temperature the evolution of hydrogen practically ceases and the sodium salt of (+)-cyanidan-3-ol is partly deposited on the wall of the reaction flask. 2.68 ml (3.85 g) of benzyl bromide are then added dropwise and this causes a slight exothermic reaction. 30 minutes later the reaction mixture becomes clear and it is agitated for a further hour at ambient temperature. The reaction solution is then poured dropwise, while stirring, into 300 ml of a cold 10% aqueous solution of sodium chloride. The precipitate formed is filtered off, dried in vacuo at 80° C., then recrystallised from 40 ml of carbon tetrachloride. 196 g of (+) 3',4',5,7-O-tetrabenzyl-cyanidan-3-ol are obtained, that is, a yield of 60.3%.

EXAMPLE 41

The procedure is as in Example 37, except that 416 g of α-bromo-o-xylene are used instead of benzyl bromide. The residue obtained after removing the dimethylformamide is taken up in chloroform. This solution is washed with distilled water, filtered and evaporated. The residue is recrystallised from a mixture of benzene and petroleum ether (6:3 v/v). (+) 3',4',5,7-O-tetra-(2-methylbenzyl)-cyanidan-3-ol is obtained in a yield of 51%. Mp.: 88°–90° C.

EXAMPLE 42

The procedure is as in Example 37 except that 416 g of α-bromo-p-xylene is used instead of benzyl bromide. The residue obtained after removing the dimethylformamide is taken up in chloroform. This solution is washed with water, filtered and evaporated, then recrystallised from carbon tetrachloride. (+) 3',4',5,7-O-tetra-(4-methylbenzyl)-cyanidan-3-ol is obtained in a yield of 40%. Mp.: 66°–70° C.

EXAMPLE 43

The procedure is as in Example 37 except that 562 g of 2-bromobenzyl bromide are used instead of benzyl bromide. The residue obtained after removing the dimethylformamide is taken up in chloroform. This solution is washed with water, filtered and evaporated then recrystallised from a mixture of chloroform and carbon tetrachloride (40:55 v/v). The yield of (+) 3',4',5,7-O-tetra-(2-bromobenzyl)-cyanidan-3-ol is 74%. Mp.: 155°–157° C.

EXAMPLE 44

The procedure is as in Example 37 except that 181 g of methyl chloromethyl ether are used instead of benzyl bromide. The residue obtained after removing the dimethylformamide is taken up in chloroform, washed three times with water, then evaporated. Recrystallisation is carried out first of all from n-hexane then from a mixture of methanol and water (1:1 v/v). (+) 3',4',5,7-O-tetra(methoxymethyl)-cyanidan-3-ol is obtained in a yield of 40%. Mp.: 92°–93° C.

EXAMPLE 45

The procedure is as in Example 37 except that 272 g of allyl bromide are used instead of benzyl bromide. The final solution of dimethylformamide is poured into a mixture of water and crushed ice; the white precipitate formed is separated by centrifugation, and dissolved in chloroform. The $CHCl_3$ solution is washed three times with water then evaporated. The residue is recrystallised from n-hexane. The yield of (+) 3',4',5,7-O-tetra-allyl-cyanidan-3-ol is 28%. Mp.: 78.5°–80° C.

EXAMPLE 46

The procedure is as in Example 37, except that 244 g of ethyl chloroformate are used instead of benzyl bromide. The distillation residue of the dimethylformamide is taken up in chloroform and the $CHCl_3$ solution is washed several times with water then evaporated. The residue is dissolved in a mixture of methanol and water (15:5 v/v) and the impurities are precipitated. After standing for several days in the cold, the supernatant liquid is distilled and (+) 3',4',5,7,-O-tetra(ethoxycarbonyl)-cyanidan-3-ol is recovered in a yield of 52%. Mp.: approximately 65° C.

EXAMPLE 47

1.45 g of (+)-cyanidan-3-ol is dissolved in 50 ml of anhydrous acetone, 6.91 g of anhydrous potassium carbonate are added and this mixture is refluxed under a nitrogen atmosphere. A solution of 6.26 g of p-bromophenacyl bromide in 30 ml of anhydrous acetone is then added and reflux is continued, while stirring, for 3 hours. After cooling the reaction solution, the salts are filtered off, the solution is evaporated to dryness and the residue is taken up in 50 ml of chloroform. The chloroform solution is washed 3 times with 50 ml of water then the chloroform is driven off and 6.23 g of a yellow pulverulent residue are obtained. This residue is dissolved in approximately 1000 ml of ether. The insoluble part, as well as some crystals formed by cooling, are filtered off. The ether solution is then concentrated to 150 ml, which produces 2.9 g of (+) 3',4',5,7-O-tetra-(4- bromophenacyl)-cyanidan-3-ol, that is, a yield of 53.8%. This product may be recrystallised from ethanol. Mp.: 127°–129° C.

EXAMPLE 48

A 3-necked 500 ml spherical flask is fitted with a reflux condenser closed with a calcium chloride tube, a nozzle for the introduction of nitrogen which also permits a vacuum to be imposed, a separating funnel with pressure equaliser and a magnetic stirrer. A current of nitrogen is passed through and 5.4 g of a 55% suspension of NaH in oil is introduced. The suspension is washed twice with 50 ml of anhydrous hexane to remove the oil, the NaH is dried in vacuo, then a solution of 32.5 g of (+) 3',4',5,7-O-tetrabenzyl-cyanidan-3-ol in 200 ml of anhydrous THF is added. The mixture is refluxed for 2 hours and cooled on an ice bath, then a solution of 9 g of methoxymethyl chloride in 40 ml of anhydrous THF is added dropwise over the course of 45 minutes. The mixture is stirred over the ice bath for $2\frac{1}{2}$ hours. The solution is siphoned through a glass frit under nitrogen then filtered through Cellite. The filtrate is evaporated to dryness at ambient temperature in a rotary evaporator (Rotavapor). The residue is recrystallised twice from a mixture of 200 ml of acetone and 500 ml of propan-2-ol. Yield: 25.1 g (72.3%) of (+) 3',4',5,7-O-tetrabenzyl-3-O-methoxymethyl-cyanidan-3-ol. Mp.: 108°–110° C.

EXAMPLE 49

A suspension of 7.15 g of palladium chloride in 2.4 liters of methanol is hydrogenated in a 5 liter spherical flask. The majority of the methanol is decanted off and the palladium is washed four times with 4 liters of methanol and four times with 200 ml of ethyl acetate. After the last decantation, the palladium is left under a thin layer of ethyl acetate. A solution of 20 g of (+) 3',4',5,7-O-tetrabenzyl-3-O-methoxymethylcyanidan-3-ol in 2.4 liters of ethyl acetate is added; the hydrogenation consumes 3.6 liters of hydrogen and lasts for 5 hours. The palladium is then filtered off and washed twice with 200 ml of ethyl acetate. The combined ethyl acetate solutions are evaporated to dryness, 700 ml of ethanol are added to the residue, the mixture is evaporated to approximately 100 ml and this treatment is repeated once more, then twice with 700 ml of water. The residue is dried to constant weight in vacuo at ambient temperature. The yield of (+) 3-O-methoxymethyl-cyanidan-3-ol is quantitative. Mp.: 106°–109° C.

EXAMPLE 50

42.5 g (37.9 ml) of boron trifluoride etherate in 50 ml of diglyme freshly distilled over sodium are introduced into a three-necked spherical flask A, fitted with a nozzle for the introduction of nitrogen, a dropping funnel and an evacuation nozzle. A solution of 7.65 g of sodium borohydride in 250 ml of diglyme is placed in the dropping funnel.

A second spherical flask B with four necks is fitted with a dropping funnel, a downwardly extending frit connected to the evacuation nozzle of flask A, an independent nozzle for the introduction of nitrogen and a reflux condenser of which the upper end is connected to a washing bottle containing acetone by way of a U-tube containing blue silica gel. A solution of 28 g of (+) 3',4',5,7-O-tetrabenzyl-3-O-(2-cyanoethyl)-cyanidan-3-ol in 500 ml of anhydrous THF freshly distilled over sodium is placed in this flask B. The two flasks A and B are equipped with a magnetic stirrer; the contents of flask A are stirred vigorously whilst the contents of flask B are mixed gently. A current of dry nitrogen is passed through which flushes in succession flask A, flask B, the condenser of flask B, the U-tube and the washing bottle, from where it leaves and passes into the casing. The solution of sodium borohydride is introduced dropwise into flask A over the course of $1\frac{1}{2}$ hours and on contact with boron trifluoride etherate produces boron hydride $B_2H_6$ which is taken along by the nitrogen current into flask B where it reduces the 2-cyanoethyl grouping to 3-aminopropyl. The mixture is left to react for $5\frac{1}{2}$ hours after the introduction of sodium borohydride is complete. 100 ml of absolute ethanol are then introduced through the dropping funnel of flask B; gases are evolved, the evolution stopping after a few minutes. The reaction liquor of flask B is then distilled in vacuo in a rotary evaporator (Rotavapor) at a temperature below 30° C. The residue is dissolved in 200 ml of boiling butan-2-ol and left overnight at 4° C.; an oil forms. The butan-2-ol is decanted off and this treatment with butan-2-ol is repeated four times.

The combined butanol extracts are evaporated in a rotary evaporator (Rotavapor) and the residue is dried under a high vacuum over $P_2O_5$ for 24 hours to constant weight. The yield of (+) 3',4',5,7-O-tetrabenzyl-3-O-(3-aminopropyl)-cyanidan-3-ol is 12.9 g, that is, 45.6%. Mp: 93°–95° C.

EXAMPLE 51

A suspension in 700 ml of freshly distilled dimethylformamide of 65.5 g of a 55% dispersion of sodium hydride in oil (36 g of NaH) is prepared under nitrogen and while stirring vigorously. This suspension is brought to a temperature of between −5° and 0° C. by means of a cooling bath. A solution of 650 g of (+) 3',4',5,7-O-tetrabenzyl-cyanidan-3-ol in 3800 ml of freshly distilled dimethylformamide is added slowly to this cooled suspension in such a manner that the temperature of the suspension remains between −5° and 0° C. 15 minutes after this solution has been introduced, 178.5 ml, that is, 257 g, of benzyl bromide are added over the course of approximately 45 minutes in such a manner that the temperature always remains below 0° C. This temperature is then maintained for approximately 30 minutes, then it is allowed to rise to ambient temperature while stirring. The dimethylformamide is removed by distillation under a medium vacuum at 60° C. in a rotary evaporator (Rotavapor), and the residue is taken up in 3 liters of chloroform at ambient temperature, then washed three times with 2 liters of distilled water; the chloroform solution is filtered on a fluted filter then evaporated. The residue is taken up in 1750 ml of hot benzene and petroleum ether (BP 30°–45° C.) is slowly added, while heating and stirring, until the mixture becomes turbid (approximately 1 liter of petroleum ether is necessary). Practically pure (+) 3,3',4',5,7-O-pentabenzyl-cyanidan-3-ol is obtained by cooling in a yield of 710 g, that is, 96%. Mp.: 119°–121° C.

EXAMPLE 52

0.96 g of a 55% dispersion of sodium hydride in oil (0.53 g of NaH) is introduced into a 3-necked 50 ml spherical flask fitted with a 25 ml dropping funnel with pressure equaliser, a nitrogen inlet and a condenser closed with a calcium chloride tube, and the whole is dried by heating under a current of nitrogen. After cooling, whilst maintaining a weak current of nitrogen, 10 ml of freshly distilled dimethyl sulphoxide are added and the mixture is stirred at ambient temperature by means of a magnetic stirrer. A solution of 1.45 g of (+) cyanidan-3-ol in 15 ml of freshly distilled dimethyl sulphoxide is then added dropwise from the dropping funnel, while stirring at ambient temperature. Hydrogen is evolved. 30 minutes after the addition of the (+)-cyanidan-3-ol solution is complete, a solution of 2.74 ml (2.99 g) of methoxyethoxymethyl chloride in 10 ml of freshly distilled dimethyl sulphoxide is introduced slowly by means of the dropping funnel. 30 minutes after the addition of methoxyethoxymethyl chloride solution is complete the reaction solution is poured into 150 ml of water saturated with sodium chloride and the pH is adjusted to 7; a brownish-black caked precipitate is obtained and this is extracted 3 times with 100 ml of toluene each time. The solutions thus obtained are combined and washed 3 times with 50 ml of water each time, then the toluene is evaporated off. 2.88 g of oily brownish-red residue are recovered. This oil is extracted ten times with 100 ml of n-hexane each time under reflux. The combined n-hexane solutions product, after cooling, 1.53 g of (+) 3′,4′,5,7-O-tetra(methoxyethoxymethyl)-cyanidan-3-ol in the form of a yellowish oil. Decomposition at 150°/0.02 mmHg.

EXAMPLE 53

A solution of 52 g of (+) 3′,4′,5,7-O-tetrabenzyl-cyanidan-3-ol in 300 ml of anhydrous pyridine is introduced into a 4-necked 500 ml spherical flask, fitted with a dropping funnel with pressure equaliser, a condenser closed with a calcium chloride tube, a nozzle for the introduction of nitrogen and a magnetic stirrer. While stirring under nitrogen, 18 g of ethyl chloroformate are added dropwise through the dropping funnel, and the mixture is heated at 60° C. for 7 hours. The mixture is allowed to cool then mixed with 500 ml of a mixture of water and crushed ice. The precipitate formed is filtered off then mixed with 500 ml of aqueous 0.5N NaHCO$_3$. The precipitate is filtered off, thoroughly washed with water, then dried in vacuo overnight. The solid is dissolved in 550 ml of acetone, filtered and the filtrate is heated under gentle reflux with 3.3 l of ethanol. After the mixture has been left at ambient temperature for 2 days, the precipitate is filtered off and recrystallised from a mixture of 250 ml of acetone and 1.5 l of ethanol. After drying, (+) 3′,4′,5,7-O-tetrabenzyl-3-O-ethoxycarbonyl-cyanidan-3-ol is obtained in a yield of 42 g, that is, 73%. Mp.: 83°–84° C.

EXAMPLE 54

The palladium black is prepared from 4 g of palladium chloride as in Example 1. A solution of 15 g (0.021 mole) of (+) 3′,4′,5,7-O-tetrabenzyl-3-O-ethoxycarbonyl-cyanidan-3-ol in 600 ml of ethyl acetate is added. Hydrogenation is carried out for 2½ hours and 2.33 l of hydrogen are consumed. The palladium is filtered off, washed twice with 200 ml of ethyl acetate and the combined solutions of ethyl acetate are evaporated to dryness. 500 ml of ethanol are added to the residue and evaporated to a volume of approximately 50 ml, then 200 ml of ethanol and 250 ml of water are added and evaporated to a volume of 50 ml, and 500 ml of water are added and evaporated to a volume of 50 ml. This operation is repeated then the precipitate that has formed is filtered off and dried under a high vacuum to constant weight. 7.4 g (97%) of (+) 3-O-ethoxycarbonyl-cyanidan-3-ol are obtained. Mp.: 123°–124° C.

EXAMPLE 55

A solution of 65 g of (+) 3′,4′,5,7-O-tetrabenzyl-cyanidan-3-ol in 350 ml of anhydrous pyridine is introduced into a 3-necked 750 ml spherical flask fitted with a dropping funnel with pressure equaliser, a condenser closed with a calcium chloride tube, a nozzle for the introduction of nitrogen and a magnetic stirrer. The solution is heated to 60° C., then, while stirring under nitrogen, 31 g of phenylacetyl chloride are added dropwise. The mixture is left to react under the same conditions for 6 hours, then the reaction mixture is allowed to cool and poured onto 1 kg of crushed ice. The whole is mixed until the ice has melted, and the water is decanted off to isolate the caked precipitate that has formed. The precipitate is washed twice with 1 liter of aqueous 1N NaHCO$_3$, then twice with one liter of water. It is dried in vacuo overnight and the product is recrystallised from 1.2 l of methoxyethanol. After drying, (+) 3′,4′,5,7-O-tetrabenzyl-3-O-phenylacetyl-cyanidan-3-ol is obtained in a yield of 57.4 g (75%). Mp.: 83°–85° C.

EXAMPLE 56

6.5 g of (+) 3′,4′,5,7-O-tetrabenzyl-cyanidan-3-ol, 1.9 g of 2,4-dinitrofluorobenzene, 3 g of potassium fluoride, 500 mg of 18-Crown-6 and 100 ml of anhydrous tetrahydrofuran are introduced into a 2-necked 250 ml spherical flask fitted with a condenser closed with a calcium chloride tube, a nozzle for the introduction of nitrogen and a magnetic stirrer. The mixture is refluxed while stirring under nitrogen for 24 hours. After cooling and adding 250 ml of toluene, the mixture is washed 4 times with 300 ml of a saturated aqueous solution of NaCl. The organic phase is dried over MgSO$_4$ then the solvents are removed by evaporation in vacuo. The residue is washed twice with 25 ml of petroleum ether (BP. 30°–45° C.), dissolved in 65 ml of chloroform, then this solution is added slowly to 325 ml of boiling absolute ethanol. The mixture is allowed to cool and an oil is obtained which is separated by decantation. It is washed with a little ethanol then dried under a high vacuum for 24 hours. 5.1 g (62%) of (+) 3′,4′,5,7-O-tetrabenzyl-3-O-(2,4-dinitrophenyl)-cyanidan-3-ol, which has solidified, is obtained. Mp.: 61°–62° C.

EXAMPLE 57

400 mg of a 55% dispersion of sodium hydride in oil are introduced into a 3-necked 50 ml spherical flask fitted with a reflux condenser closed with a calcium chloride tube, a nozzle for the introduction of nitrogen, a membrane closure and a magnetic stirrer. A strong current of nitrogen is passed through for 5 minutes then the nitrogen supply is reduced and 5 ml of anhydrous tetrahydrofuran freshly distilled over sodium are added. The mixture is heated to 40° C. then, by means of a syringe, first of all a solution of 0.5 ml of freshly distilled methyl iodide in 10 ml of anhydrous tetrahydrofuran then a solution of 2.3 g of (+) 3′,4′,5,7-O-tetramethoxymethyl-cyanidan-3-ol in 10 ml of anhydrous tetrahydrofuran are added. The reaction mixture is agitated at 40° for 1 hour then filtered. 20 ml of toluene and 40 ml of water are added to the filtrate, which is agitated and then left to stand before separating the organic phase which is washed again with 10 ml of water. The combined aqueous phases are extracted with 30 ml of methylene chloride. The combined organic extracts are then dried over magnesium sulphate, filtered, then evaporated in a rotary evaporator (Rotavapor), which produces an oil that does not solidify. This residual oil, dissolved in 55 ml of methanol, is treated with activated carbon then, after evaporating the methanol, the oil is extracted twice with 25 ml of petroleum ether (BP 50°–70° C.) under heat. The combined petroleum ether fractions are evaporated in a rotary evaporator (Rotavapor) at ambient temperature and the residual oil, which comprises (+) 3′,4′,5,7-O-tetra(methoxymethyl)-3-O-methyl-cyanidan-3-ol is dried under a high vacuum to constant weight. IR (Nujol) $\nu$ (cm$^{-1}$): 2920, 1615, 1590, 1507, 1494, 1440, 1400, 1260, 1220, 1155, 1070, 1000, 920, 822.

EXAMPLE 58

A 1 liter spherical flask is fitted with a rotary agitator, a thermometer, a condenser closed with a silica gel tube, a nitrogen inlet, and a 250 ml dropping funnel and the apparatus is previously dried at 100° in vacuo overnight. The flask is heated on a thermostatically-controlled oil bath. 110 g of dry potassium carbonate are then introduced under a slight current of nitrogen, then 250 ml of dry dimethylformamide are added. A solution of 29.0 g of (+)-cyanidan-3-ol in 250 ml of dry dimethylformamide which has been dried overnight on a molecular sieve (4 Å) is then poured in and finally 71.25 ml of benzyl bromide diluted in 100 ml of dry dimethylformamide are added. The mixture is heated at 100° for 5½ hours while stirring and passing through nitrogen. The final suspension is filtered hot, the filtrate evaporated in vacuo in a rotary evaporator at 80° and taken up in 250 ml of chloroform. The chloroform solution is filtered and transferred to a 1 liter separating funnel where it is washed 3 times with 250 ml of water each time, then it is dried over magnesium sulphate and evaporated to dryness. The residue is taken up in 750 ml of carbon tetrachloride under reflux. The caked brown residue is separated and allowed to crystallise while agitating at normal temperature with intermittent cooling in a refrigerator. 31.2 g of a product identical to that obtained in Example 37 is recovered. Mp.: 144°–145° C.

EXAMPLE 59

Palladium black is prepared from 15 g of palladium chloride as in Example 1. A solution of 40 g of (+) 3′,4′,5,7-O-tetrabenzyl-3-O-phenylacetylcyanidan-3-ol in 2.25 l of ethyl acetate is added. The mixture is hydrogenated for 3 hours; 1.25 l of hydrogen are consumed. The palladium is filtered off and washed twice with 300 ml of ethyl acetate, then the combined ethyl acetate solutions are evaporated to dryness under reduced pressure. 500 ml of ethanol are added to the residue and evaporated under reduced pressure to a volume of approximately 50 ml; this operation is repeated. 250 ml of ethanol and 250 ml of water are then added, then evaporated, still under reduced pressure, to 50 ml. 500 ml of water are added and evaporated under the same conditions to a volume of 50 ml, then a further 500 ml of water are added and evaporated under reduced pressure. The residue is dried to constant weight under a high vacuum overnight, which yields (+) 3-O-phenylacetylcyanidan-3-ol. Mp.: 102°–103° C.

EXAMPLE 60

A solution of 24.8 g of nicotinoyl chloride in 100 ml of anhydrous pyridine is introduced into a 3-necked 250 ml spherical flask, fitted with a dropping funnel with pressure equaliser, a condenser closed with a calcium chloride tube, a nozzle for the introduction of nitrogen and a magnetic stirrer. 56 g of (+) 3′,4′,5,7-O-tetrabenzyl-cyanidan-3-ol in four portions, one of 26 g and three of 10 g, are added dropwise while stirring and under nitrogen, leaving an hour between the addition of each portion. The mixture is heated at 60° for 20 hours. After cooling the solution is poured into 1 kg of crushed ice and mixed with a "mixer" until the ice has melted. The liquid is decanted off and a caked precipitate remains. This is washed twice with water, twice with 1N sodium bicarbonate, then twice with water while mixing with a "mixer". The insoluble portion, while still cakes, is dried in vacuo overnight. 120 ml of acetone are added, the mixture is stirred for 10 minutes and left for 2 hours at −30°. The precipitate is filtered off and retreated with acetone in the same manner. The product is recrystallised from 950 ml of methoxyethanol and 1.9 l of absolute ethanol. (+) 3′,4′,5,7-O-tetrabenzyl-3-O-nicotinoyl-cyanidan-3-ol is obtained. Mp.: 137°–138° C.

EXAMPLE 61

1.5 g of (+) 3′,4′,5,7-O-tetrabenzyl-3-O-nicotinoyl-cyanidan-3-ol is hydrogenated in the presence of 100 ml of anhydrous ethanol, 300 mg of trifluoromethanesulphonic acid and 1.0 g of 10% palladium on activated carbon, while heating at 50°. The reaction lasts for 5 hours and 500 ml of hydrogen are consumed. The mixture is allowed to cool, is then filtered and the filtrate evaporated to dryness. 100 ml of distilled water are added and evaporated to a volume of approximately 10 ml. This operation is repeated 3 times then the product is lyophilised. A quantitative yield of (+) 3-O-(3-piperidylcarbonyl)-cyanidan-3-ol trifluoromethanesulphonate is obtained. (Mixture of the 2 diastereoisomers) Mp.: 125°–130° (not sharp).

EXAMPLE 62

5.2 g of (+) 3′,4′,5,7-O-tetrabenzyl-cyanidan-3-ol and 200 ml of toluene are placed in a 500 ml spherical flask fitted with a condenser and a "vibromisher". The mixture is heated to approximately 90° until dissolution occurs, then 200 ml of a 50% solution of sodium hydroxide, 2.7 g of tetrabutylammonium bisulphate and 3.0 g of 2-cyclohexylethyl bromide are added. The temperature is maintained at 90° for 10 hours while agitating vigorously, then 1.5 g of 2-cyclohexylethyl bromide are added. The temperature is again maintained at 90° for 15 hours while agitating vigorously then the mixture is allowed to cool to ambient temperature. The two phases are separated and the organic phase is washed three times with 250 ml of water. The toluene is dried over magnesium sulphate then evaporated to dryness. The residue is taken up in 60 ml of absolute ethanol heated to 60°, agitated for 15 minutes, then the insoluble part is filtered off hot. This precipitate is dried in vacuo then recrystallised from 80 ml of methoxyethanol. (+) 3′,4′,5,7-O-tetrabenzyl-3-O-(2-cyclohexylethyl)-cyanidan-3-ol is obtained. Mp.: 110°.

EXAMPLE 63

1.0 g of (+) 3′,4′,5,7-O-tetrabenzyl-3-O-(2-cyclohexylethyl)-cyanidan-3-ol, dissolved in 90 ml of ethyl acetate is hydrogenated in the presence of 400 mg of 10% palladium on activated carbon. 180 ml of hydrogen are consumed. The mixture is filtered then the solvent and the toluene formed are evaporated. The oily residue is dissolved in 100 ml of ethanol, evaporated almost to dryness, then 100 ml of ethanol are added again and evaporated again. 50 ml of ethanol and 50 ml of water are added and the mixture is evaporated. The residue is taken up in 150 ml of water which is evaporated to dryness, and the residue is dried over phosphorus pentoxide under a high vacuum to constant weight. A quantitative yield of (+) 3-O-(2-cyclohexylethyl)-cyanidan-3-ol is obtained. Mp.: 99°–102°.

EXAMPLE 64

65 g of (+) 3',4',5,7-O-tetrabenzyl-cyanidan-3-ol and 2 l of toluene are placed in a 6 liter spherical flask fitted with a condenser and a mechanical agitator. Heating is carried out until dissolution occurs, then 1.5 l of a 50% sodium hydroxide solution, 34 g of tetrabutylammonium bisulphate and 40 g of 3-phenylpropyl bromide are added. The mixture is heated at 50° while stirring vigorously for 48 hours, then the solution is allowed to cool to ambient temperature. The two phases are separated and the organic phase is washed three times with 1 l of water. The toluene is dried over magnesium sulphate then evaporated. The oily residue is washed with 200 ml of petroleum ether then with 150 ml of anhydrous ethanol. The product is recrystallised from 600 ml of methoxyethanol. (+) 3',4',5,7-O-tetrabenzyl-3-O-(3-phenylpropyl)-cyanidan-3-ol is obtained. Mp.: 96°–97°.

EXAMPLE 65

40.0 g of (+) 3',4',5,7-O-tetrabenzyl-3-O-(3-phenylpropyl)-cyanidan-3-ol dissolved in 3 l of ethyl acetate are hydrogenated in the presence of 16 g of 10% palladium on activated carbon. The reaction lasts 6 hours and 6.2 l of hydrogen are consumed. The mixture is filtered, then the solvent and the toluene formed are evaporated. 250 ml of water are added, and the mixture is stirred and evaporated in vacuo until the solid coagulates. Filtration is carried out and the precipitate is washed thoroughly with water. After drying to constant weight, (+) 3-O-(3-phenylpropyl)-cyanidan-3-ol is obtained. Mp.: 190°–192°.

EXAMPLE 66

52 g of (+) 3',4',5,7-O-tetrabenzyl-cyanidan-3-ol and 500 ml of toluene are introduced into a 3 liter spherical flask fitted with a condenser and a mechanical agitator. The mixture is heated until dissolution occurs, then 187 g of propyl chloride, 750 ml of 50% sodium hydroxide solution and 6.8 g of tetrabutylammonium bisulphate are added. This is heated at 50° while stirring vigorously for 24 hours, then the solution is allowed to cool to ambient temperature. The two phases are separated and the organic is washed three times with 500 ml of a saturated aqueous solution of sodium chloride. The organic phase is dried over magnesium sulphate then the solvent is evaporated. 100 ml of carbon tetrachloride are added then evaporated to dryness. The product is recrystallised from a mixture of 1.8 l of ethanol and 0.3 l of acetone. (+) 3',4',5,7-O-tetrabenzyl-3-O-propyl-cyanidan-3-ol is obtained. Mp.: 92°–93°.

EXAMPLE 67

Palladium black is prepared from 12 g of palladium chloride as described in Example 1. A solution of 41.6 g of (+) 3',4',5,7-O-tetrabenzyl-3-O-propylcyanidan-3-ol in 1.8 l of ethyl acetate is added. Hydrogenation is carried out for 6 hours and 6.25 l of hydrogen are consumed. The palladium is filtered off. It is washed twice with 200 ml of ethyl acetate. The combined solutions are evaporated to dryness. 500 ml of water are added then evaporated under reduced pressure to a volume of approximately 50 ml. This operation is repeated 3 times then the product is lyophilised. A quantitative yield of (+) 3-O-propylcyanidan-3-ol is obtained. Mp.: 94°–96°.

EXAMPLE 68

A solution of 65.0 g of (+) 3',4',5,7-O-tetrabenzyl-cyanidan-3-ol in 500 ml of anhydrous pyridine is placed in a 4-necked 1 l spherical flask fitted with a condenser closed with a calcium chloride tube, a dropping funnel with pressure equaliser, an agitator and a nozzle for the introduction of nitrogen. 34.5 g of diethyl chlorophosphate are then added dropwise under nitrogen. The mixture is agitated under nitrogen at ambient temperature for 8 hours. The reaction mixture is poured into 1 liter of a mixture of ice and water and the whole is mixed. The water is decanted off from the caked mass that has formed. The latter is washed five times with 500 ml of water each time, then it is left in vacuo overnight at 40°, during the course of which it solidifies. The product is recrystallised from 720 ml of carbon tetrachloride and 2.8 l of petroleum ether. Diethyl phosphate and 2R,3S 3',4',5,7-tetrabenzyloxy-flavan-3-yl phosphate are obtained after drying under a high vacuum to constant weight. Mp.: 96°.

EXAMPLE 69

Palladium black is prepared from 13 g of palladium chloride in the manner described in Example 1. A solution of 30.0 g of diethyl phosphate and 2R,3S 3',4',5,7-tetrabenzyloxy-flavan-3-yl phosphate in 1.3 l of ethyl acetate are added. The hydrogenation is carried out for 3 hours and 3.9 l of hydrogen are consumed. The palladium is filtered off and washed twice with 200 ml of ethyl acetate. The combined solutions are evaporated to dryness. 750 ml of water are added to the residue and evaporated under reduced pressure to a volume of approximately 100 ml. This operation is repeated twice then the product is lyophilised. Diethyl phosphate and 2R,3S 3',4',5,7-tetrahydroxy-flavan-3-yl phosphate are obtained. Mp.: 121°–123°.

EXAMPLE 70

1.30 g of (+) 3',4',5,7-O-tetrabenzyl-cyanidan-3-ol, 100 ml of toluene, 100 ml of a 50% aqueous sodium hydroxide solution, 500 mg of dimethyl sulphate and 68 mg of tetrabutylammonium bisulphate are placed in a 500 ml spherical flask fitted with a condenser and a mechanical agitator. The mixture is heated at 50° for one hour while stirring vigorously, then it is allowed to cool to ambient temperature and the two phases are separated. The organic phase is washed 3 times with 100 ml of water then dried over magnesium sulphate before evaporating the solvent. The residue is recrystallised from 13 ml of methoxyethanol. (+) 3',4',5,7-O-tetrabenzyl-3-O-methyl-cyanidan-3-ol, identical to the product in Example 19, is obtained. Mp.: 124°–125°.

EXAMPLE 71

500 mg of palladium black, 120 ml of ethanol, 650 mg of (+) 3',4',5,7-O-tetrabenzyl-cyanidan-3-ol and 60 ml of cyclohexene are placed in a 250 ml spherical flask. While stirring, the reaction mixture is refluxed for 4 hours. Thin layer chromatography over silica gel Merck 60 (mobile phase: ethyl acetate/chloroform/formic acid 5:5:1 v/v/v) shows that the removal of the benzyl groups is quantitative. At ambient temperature the palladium is removed by filtration and the filtrate is distilled under reduced pressure. The residue is recrystallised from water; it is (+)-cyanidan-3-ol. Mp.: 207°-210°.

EXAMPLE 72

A 4-necked 500 ml spherical flask is fitted with an efficient mechanical agitator, a 250 ml dropping funnel, a calcium chloride tube and a tube for the introduction of nitrogen. The whole apparatus is dried and nitrogen is circulated through it before introducing 100 ml of anhydrous DMF. This is cooled to −3° C. and 9.28 g of a 55% dispersion of NaH in oil is added. While agitating, a solution of 14.5 g of (+)-cyanidan-3-ol in 200 ml of anhydrous DMF, then 1.698 g of tetra-n-butylammonium bisulphate are introduced in succession and agitation is maintained for 1 hour at 0° C. Within 15 minutes a solution of 25.9 ml of benzyl chloride in 25 ml of anhydrous DMF is added and the mixture is agitated for 30 minutes at 0° C. then, while agitating still, the temperature is allowed to rise to ambient temperature (25° C.) at which the reaction mixture is maintained for 24 hours while agitating vigorously. The reaction liquor is then filtered on a fluted filter and the filtrate is evaporated under reduced pressure producing a residue which is taken up in 250 ml of chloroform. The chloroform solution is washed 4 times with 250 ml of distilled water, then, after drying over anhydrous magnesium sulphate and filtering, the chloroform is evaporated under reduced pressure. The residue is washed with 50 ml of hexane then dried to constant weight. The mass of 37.4 g thus obtained is dissolved under heat in 500 ml of carbon tetrachloride, the solution is filtered hot and by cooling to ambient temperature then successively concentrating to 350 ml and 150 ml, 23.6 g (+) 3',4',5,7-O-tetrabenzyl-cyanidan-3-ol, identical to the product of Example 37, are obtained.

EXAMPLE 73

The procedure is as in Example 58, except that after the introduction of the solution of (+)-cyanidan-3-ol in DMF, 13.22 g of 18-Crown-6 are added and the benzyl bromide is replaced by 69 ml of benzyl chloride. The mixture is then heated at 60° C. for 20 hours while stirring vigorously.

45.5 g of (+) 3',4',5,7-O-tetrabenzyl-cyanidan-3-ol, identical to that of Example 37, are obtained.

EXAMPLE 74

The procedure is as in Example 73, except that 18-Crown-6 is replaced by 16.98 g of tetra-n-butylammonium bisulphate.

44.5 g of (+) 3',4',5,7-O-tetrabenzyl-cyanidan-3-ol, identical to that in Example 37, are obtained.

EXAMPLE 75

130 g of (+) 3',4',5,7-O-tetrabenzyl-cyanidan-3-ol, 250 g of 1-chloroheptane and 25 g of tetrabutylammonium bisulphate are introduced into a 5 l spherical flask fitted with a condenser and a mechanical agitator. 3.75 l of a 50% NaOH solution are added then the mixture is heated at 50° C., while agitating vigorously, for 6 hours. It is allowed to cool to ambient temperature, 1.25 l of dichloromethane are added and the two phases are separated. The organic phase is washed three times with 750 ml of water, dried over MgSO₄, then the solvent is evaporated off. 4 l of petroleum ether (boiling point 40°-60°) are then added to the residue and the mixture is agitated overnight. The mixture is cooled to −20° C. for ½ hour, and the solid is filtered off and washed with 500 ml of petroleum ether. After drying, recrystallisation is carried out twice from a mixture of 1.5 l of ethanol and 400 ml of ethyl acetate. After drying to constant weight in vacuo, 132 g of (+) 3',4',5,7-O-tetrabenzyl-3-O-heptyl-cyanidan-3-ol are obtained. M.p.: 65° C.

EXAMPLE 76

52 g of (+) 3',4',5,7-O-tetrabenzyl-cyanidan-3-ol and 650 ml of toluene are introduced into a 3 l spherical flask fitted with a condenser and a mechanical agitator. The mixture is heated until dissolution occurs, then 115 g of 1-chlorododecane, 27 g of tetrabutylammonium bisulphate and 750 ml of a 50% NaOH solution are added. The mixture is heated at 50° C. for 4 days while agitating vigorously, then it is allowed to cool to ambient temperature. The two phases are separated and the organic phase is washed three times with 500 ml of water. It is dried over MgSO₄, then the solvent is evaporated off. The residue is mixed twice with 500 ml of petroleum ether (boiling point 40°-60° C.). After filtering and drying, the product is recrystallised from 800 ml of acetone and 3.2 l of ethanol. After drying to constant weight in vacuo, 54 g of (+) 3',4',5,7-0-tetrabenzyl-3-O-dodecyl-cyanidan-3-ol are obtained. Mp.: 98°-99° C.

EXAMPLE 77

A mixture of 26 g of (+) 3',4',5,7-O-tetrabenzyl-cyanidan-3-ol, 73 g of 1-chlorohexadecane and 5 g of tetrabutylammonium bisulphate are introduced into a 1 l spherical flask fitted with a condenser and a mechanical agitator. 750 ml of a 50% aqueous NaOH solution are added then the mixture is heated at 50° C. while agitating vigorously for 24 hours. The mixture is allowed to cool to ambient temperature then 250 ml of dichloromethane are added. The two phases are separated and the organic phase is washed with 250 ml of water. The solvent is evaporated, 375 ml of ethanol are added and agitation is carried out for 2 hours. The mixture is cooled to −10° C., the solid is filtered off and washed with 50 ml of ethanol and dried in vacuo. The product is recrystallised from 300 ml of ethanol and 70 ml of ethyl acetate, then dried to constant weight in vacuo. 30 g of (+) 3',4',5,7-0-tetrabenzyl-3-O-hexadecyl-cyanidan-3-ol are obtained. Mp.: 88°-89° C.

EXAMPLE 78

52 g of (+) 3',4',5,7-O-tetrabenzyl-cyanidan-3-ol, 162 g of 1-chlorooctadecane and 10 g of tetrabutylammonium bisulphate are introduced into a 3 l spherical flask fitted with a mechanical agitator and a condenser. 1.5 l of a 50% NaOH solution are added and the mixture is heated at 50° C. for 28 hours while agitating vigorously. The mixture is allowed to cool to ambient temperature, 500 ml of dichloromethane are added and the two phases are separated. The organic phase is washed with 500 ml of water. An emulsion is formed and the two phases are separated by filtration on a phase separator paper. The organic phase is dried over MgSO₄, then the solvent is evaporated off. 750 ml of ethanol are added and agitation is carried out for 2 hours. The solid is filtered off and washed with 100 ml of ethanol. The product is recrystallised twice from a mixture of 600 ml of ethanol and 260 ml of ethyl acetate. After drying to constant weight in vacuo, 60 g of (+) 3',4',5,7-O-tetrabenzyl-3-O-octadecyl-cyanidan-3-ol are obtained. Mp.: 86° C.

EXAMPLE 79

56 g of (+) 3',4',5,7-O-tetrabenzyl-3-O-heptyl-cyanidan-3-ol dissolved in 2.25 l of ethyl acetate are hydrogenated in a 5 l spherical flask in the presence of 40 g of 10% palladium on activated carbon. The catalyst is filtered off and washed twice with 300 ml of ethyl acetate. The combined solutions are evaporated to dryness, the residue is triturated in 250 ml of water, then the water is evaporated to a volume of approximately 50 ml. This operation is repeated twice before evaporating to dryness, then the residue is dried to constant weight under a high vacuum over $P_2O_5$. 25 g of (+) 3-O-heptyl-cyanidan-3-ol are obtained. Mp.: 157°–159° C.

EXAMPLE 80

40 g of (+) 3',4',5,7-O-tetrabenzyl-3-O-dodecyl-cyanidan-3-ol dissolved in 3 l of ethyl acetate are hydrogenated in a 6 l spherical flask in the presence of 20 g of 10% palladium on activated carbon. The reaction lasts 6 hours and 6.2 l of hydrogen are consumed. The catalyst is filtered off and washed twice with 300 ml of ethyl acetate. The combined solutions are evaporated to dryness then the oily residue is taken up in 1 l of ethanol. The solvent is evaporated to a volume of approximately 50 ml then 1 l of water is added and evaporated to a volume of approximately 50 ml. 1 l water is added again and evaporated to a volume of approximately 100 ml and the solid is filtered off and washed with water. After drying to constant weight under a high vacuum over $P_2O_5$, 21.5 g of (+) 3-O-dodecyl-cyanidan-3-ol are obtained. Mp.: 158°–160° C.

EXAMPLE 81

26.3 g of (+) 3',4',5,7-O-tetrabenzyl-3-O-hexadecyl-cyanidan-3-ol dissolved in 1.5 l of ethyl acetate are hydrogenated in a 3 l spherical flask in the presence of 16 g of 10% palladium on activated carbon. The catalyst is filtered off and washed twice with 100 ml of ethyl acetate. The combined solutions are evaporated to dryness then the residue is treated with 5 g of activated carbon in 100 ml of ether for 1 hour. The mixture is filtered, the filtrate is evaporated to dryness, the residue is triturated in 60 ml of water and the water evaporated to a volume of approximately 10 ml. This operation is repeated twice then the mixture is evaporated to dryness and the residue is dried to constant weight under a high vacuum over $P_2O_5$. 10.5 g of (+) 3-O-hexadecyl-cyanidan-3-ol are obtained. Mp.: 152°–154° C.

EXAMPLE 82

83.7 g of (+) 3',4',5,7-O-tetrabenzyl-3-O-octadecyl-cyanidan-3-ol dissolved in 4.5 l of ethyl acetate are hydrogenated in an 8 l spherical flask in the presence of 48 g of 10% palladium on activated carbon. The catalyst is filtered off and washed twice with 400 ml of ethyl acetate. The combined solutions are evaporated to dryness. The residue is recrystallised from 260 ml of chloroform containing 4% of methanol. The solid obtained is triturated in 100 ml of water, then the water is evaporated to a volume of approximately 25 ml. This operation is repeated twice, the water is evaporated, then the solid is dried to constant weight under a high vacuum over $P_2O_5$. 34.1 g of (+) 3-O-octadecyl-cyanidan-3-ol are obtained. Mp.: 162°–164° C.

EXAMPLE 83

A solution of 52 g of (+) 3',4',5,7-O-tetrabenzyl-cyanidan-3-ol in 300 ml of dichloromethane, 150 ml of a 50% aqueous solution is NaOH and 6.8 g of tetrabutylammonium bisulphate are introduced in succession into a 750 ml of spherical flask fitted with a condenser and a mechanical agitator. The mixture is refluxed for 24 hours while stirring vigorously, then it is allowed to cool to ambient temperature and the two phases are separated. The organic phase is washed three times with 300 ml of water then dried over $MgSO_4$. The solvent is evaporated and the residue is recrystallised from a mixture of 2.4 l of ethanol and 1.2 l of acetone. 39 g of di(3',4',5,7-O-tetrabenzyl-cyanidan-3-yloxy)methane are obtained. Mp.: 103°–104° C.

EXAMPLE 84

Palladium black is prepared from 5 g of palladium chloride in the manner described in Example 1. A solution of 31.0 g of di(3',4',5,7-O-tetrabenzyl-cyanidan-3-yloxy)methane in 700 ml of ethyl acetate are added. Hydrogenation is carried out for 3 hours and 4.8 l of hydrogen are consumed. The palladium is filtered off, washed twice with 100 ml of ethyl acetate, then the combined solutions are evaporated to dryness. 1 l of water neutralised to pH 7 by several drops of pyridine are added to the residue. The mixture is concentrated to approximately 100 ml under reduced pressure. This operation is repeated twice, then 900 ml of pure water are added and evaporated to a volume of approximately 200 ml. The mixture is lyophilised and 12.9 g of di(-cyanidan-3-yloxy)methane are obtained. Mp.: 162°–165° C.

EXAMPLE 85

In a manner analogous to that described in the preceding Examples the following are prepared:

(+) 3,3',4',5,7-O-penta-(methoxymethyl)-cyanidan-3-ol, (+) 3,3',4',5,7-O-pentaallyl-cyanidan-3-ol, (+) 3',4',5,7-O-tetra-(trimethylsillyl)-cyanidan-3-ol, (+) 3',4',5,7-O-tetrabenzyl-3-O-[3-(N,N-dimethylamino)propyl]-cyanidan-3-ol, (+) 3-O-[3-(N,N-dimethylamino)-propyl]-cyanidan-3-ol in the form of its hydrochloride, (+) 3',4',5,7-O-tetrabenzyl-3-O-[4-(4,4-ethylenedioxy-p-fluorophenyl)-butyl]-cyanidan-3-ol, (+) 3-O-[4-(4,4-ethylenedioxy-p-fluorophenyl)-butyl]-cyanidan-3-ol, (+) 3',4',5,7-O-tetrabenzyl-3-O-(2,3-dihydroxypropyl)-cyanidan-3-ol and (+) 3-O-(2,3-dihydroxypropyl)-cyanidan-3-ol.

We claim:

1. An O-substituted derivative of (+)-cyanidan-3-ol of the formula I

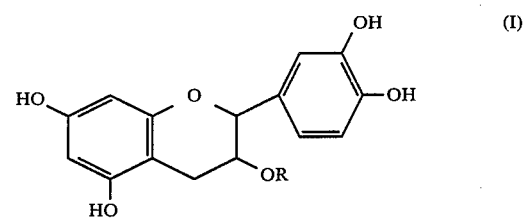

in which R represents an acyl radical of an alkanecarboxylic acid containing from 4 to 18 carbon atoms which is unsubstituted or substituted by one or more hydroxy, carboxy, ($C_{1-5}$ alkoxy)carbonyl, $C_{1-5}$ alkanoyl, amino, mono- or di($C_{1-4}$ alkyl)amino, chloro or fluoro;

cycloalkanecarboxylic acid having 3 to 6 ring carbon atoms which is unsubstituted or substituted by one, two or three, hydroxy, carboxy, $C_{1-4}$ alkoxycarbonyl, amino, mono- or di-($C_{1-4}$ alkyl)amino, chloro or fluoro;

cycloalkanealkanoic acid, the aliphatic chain thereof having 2 to 4 carbon atoms and the ring having 5 to 6 carbon atom;

phenylalkanoic acid of which the aliphatic chain contains 1 to 4 carbon atoms and of which the phenyl nucleus is unsubstituted or substituted by one or two hydroxy, $C_1$-$C_4$ alkoxy, amino, carboxy, ($C_1$-$C_4$ alkoxy)carbonyl, $C_1$-$C_4$ alkanoyl, $C_1$-$C_4$ alkanoyloxy, chloro or fluoro;

nicotinic or isonicotinic acid;

($C_1$-$C_4$ alkoxy)carbonyl;

($C_{1-4}$ alkyl)sulphonic acid, or phenylsulphonic acid unsubstituted or substituted by one or more $C_{1-4}$ alkyl, $C_{1-4}$ alkoxy or halo; carbamoyl which is unsubstituted or mono- or di-substituted by $C_1$-$C_4$ alkyl, or phenyl groups unsubstituted or substituted by hydroxy, methoxy, ethoxy, chloro or fluoro; or a phosphoric acid which is unsubstituted or substituted by dimethyl, diethyl, or monohydroxyphenyl; and pharmaceutically acceptable salts thereof.

2. A pharmaceutical composition for the prevention of hepatic necrosis, inhibition of lipoperoxidation and inhibition of collagen degradation comprising an effective amount to induce said prevention or inhibition of a compound of claim 1, and a pharmaceutically acceptable carrier.

3. A method for the prevention of hepatic necrosis, inhibition of lipoperoxidation and inhibition of collagen degradation which comprises administering to an animal an effective hepatic preventive, or liperoxidation or collagen degradation inhibitory, amount of a compound of claim 1.

4. (+) 3-O-butyryl-cyanidan-3-ol,
(+) 3-O-(3,3-dimethylbutanoyl)-cyanidan-3-ol,
(+) 3-O-(3-carboxypropionyl)-cyanidan-3-ol,
(+) 3-O-decanoyl-cyanidan-3-ol,
(+) 3-O-palmitoyl-cyanidan-3-ol,
(+) 3-O-(2-carboxycyclohexanecarbonyl)-cyanidan-3-ol,
(+) 3-O-benzoyl-cyanidan-3-ol,
(+) 3-O-(4-fluorobenzoyl)-cyanidan-3-ol,
(+) 3-O-protocatechyl-cyanidan-3-ol,
(+) 3-O-acetylsalicylyl-cyanidan-3-ol,
(+) 3-O-(2-carboxybenzoyl)-cyanidan-3-ol,
(+) 3-O-(N-phenylcarbamoyl)-cyanidan-3-ol,
(+) 3-O-methanesulphonyl-cyanidan-3-ol,
(+) 3-O-(4-methylbenzenesulphonyl)-cyanidan-3-ol,
(+) 3-O-ethoxycarbonyl-cyanidan-3-ol.

5. (+) 3-O-butyryl-cyanidan-3-ol according to claim 4.

6. (+) 3-O-(3,3-dimethylbutanoyl)-cyanidan-3-ol according to claim 4.

7. (+) 3-O-(3-carboxypropionyl)-cyanidan-3-ol according to claim 4.

8. (+) 3-O-decanoyl-cyanidan-3-ol according to claim 4.

9. (+) 3-O-palmitoyl-cyanidan-3-ol according to claim 4.

10. (+) 3-O-(2-carboxycyclohexanecarbonyl)-cyanidan-3-ol according to claim 4.

11. (+) 3-O-benzoyl-cyanidan-3-ol according to claim 4.

12. (+) 3-O-(4-fluorobenzoyl)-cyanidan-3-ol according to claim 4.

13. (+) 3-O-protocatechyl-cyanidan-3-ol according to claim 4.

14. (+) 3-O-acetylsalicylyl-cyanidan-3-ol according to claim 4.

15. (+) 3-O-(2-carboxybenzoyl)-cyanidan-3-ol according to claim 4.

16. (+) 3-O-(N-phenylcarbamoyl)-cyanidan-3-ol according to claim 4.

17. (+) 3-O-methanesulphonyl-cyanidan-3-ol according to claim 4.

18. (+) 3-O-(4-methylbenzenesulphonyl)-cyanidan-3-ol according to claim 4.

19. (+) 3-O-ethoxycarbonyl-cyanidan-3-ol according to claim 4.

* * * * *

UNITED STATES PATENT AND TRADEMARK OFFICE
CERTIFICATE OF CORRECTION

PATENT NO. : 4,617,296

DATED : October 14, 1986

INVENTOR(S) : Alban Albert, Pierre Courbat, and Andre P. Weith

It is certified that error appears in the above-identified patent and that said Letters Patent is hereby corrected as shown below:

On the cover page, in the column preceding the Abstract, change the Assignee designation from -- Ciba-Geigy Corporation, Ardsley, N.Y. -- to -- Zyma, SA, Nyon, Switzerland --.

Signed and Sealed this

Tenth Day of March, 1987

Attest:

DONALD J. QUIGG

Attesting Officer      Commissioner of Patents and Trademarks